United States Patent [19]

Sugamura et al.

[11] Patent Number: 5,510,259
[45] Date of Patent: Apr. 23, 1996

[54] HUMAN IL-2 RECEPTOR γ CHAIN MOLECULE

[75] Inventors: Kazuo Sugamura, No. 27-8, Asahigaoka 1-chome, Aoba-ku, Sendai-shi, Miyagi-ken; Toshikazu Takeshita, Sendai; Hironobu Asao, Sendai; Masataka Nakamura, Sendai; Toshiro Shimamura, Kawasaki; Manabu Suzuki, Kawasaki; Junji Hamuro, Kawasaki, all of Japan

[73] Assignees: Ajinomoto Co., Inc., Tokyo; Kazuo Sugamura, Sendai, both of Japan

[21] Appl. No.: 52,205

[22] Filed: Apr. 22, 1993

[30] Foreign Application Priority Data

Apr. 23, 1992 [JP] Japan ................................. 4-104947

[51] Int. Cl.⁶ .............................. C12N 5/00; C12N 15/00; C07H 21/04
[52] U.S. Cl. ................................. 435/240.2; 435/320.1; 435/252.3; 435/240.26; 536/23.52; 536/23.1; 536/23.5; 935/6; 935/11; 935/22; 935/23; 935/24; 935/66; 935/70; 935/72; 935/73
[58] Field of Search ........................ 435/6, 280.1, 240.2, 435/240.26, 320.1, 252.3, 252.33; 536/23.1, 23.5, 23.52; 935/1, 22, 23, 24, 6, 11, 66, 70, 72, 73

[56] References Cited

PUBLICATIONS

Takeshita et al., *Science*, vol. 257, pp. 379–382, 17 Jul. 1992.
Lymphokine Research, vol. 9, No. 4, pp. 539–542, 1990, K. Sugamura, et al., "IL–2–Induced Signal Transduction: Involvement of Tyrosine Kinase and IL–2 Receptor γ Chain".
Science, vol. 257, pp. 379–382, Jul. 17, 1992, T. Takeshita, et al., "Cloning of the γ Chain of the Human IL–2 Receptor".
The Journal of Immunology, vol. 148, No. 7, pp. 2154–2158, Apr. 1, 1992, T. Takeshita, et al., "An Associated Molecule, p. 64, with IL–2 Recteptor β Chain. Its Possible Involvement in the Formation of the Functional Intermediate–Affinity IL–2 Receptor Complex".
The Embo Journal, vol. 9, No. 12, pp. 3899–3905, 1990, S. M. Zurawski, et al., "Partial Agonist/Antagonist Mouse Interleukin–2 Proteins Indicate that a Third Component of the Receptor Complex Functions in Signal Transduction".

*Primary Examiner*—W. Gary Jones
*Assistant Examiner*—Bradley Lounsbury Sisson
*Attorney, Agent, or Firm*—Oblon, Spivak, McClelland, Maier & Neustadt

[57] ABSTRACT

The present invention relates to an IL-2 receptor γ chain molecule, a DNA-sequence encoding the IL-2 receptor γ chain molecule, a vector possessing said DNA-sequence, a cell transformed with said vector, a method for the production of an IL-2 receptor γ chain molecule by culturing of said cell, an immune response regulatory agent comprising an Il-2 receptor γ chain molecule and an antibody to an IL-2 receptor γ chain molecule.

Both the Il-2 receptor γ chain molecule and the antibody to the IL-2 receptor γ chain molecule are very useful immune response regulatory agents.

18 Claims, 5 Drawing Sheets

Probe No.1

```
ATACTGACGC CGAATGG
    TT A   A    A
    C     T    T
          C    C
```

Probe No.1
ATACTGACGC CGAATGG
  TT A   A    A
  C     T    T
        C    C        *FIG. 1A*

Probe No.2
ATACTGACGC CGAACGG
  TT A   A    A
  C     T    T
        C    C        *FIG. 1B*

Probe No.3
ATACTTACGC CGAATGG
  T C   A    A
  C     T    T
        C    C        *FIG. 1C*

Probe No.4
ATACTTACGC CGAACGG
  T C   A    A
  C     T    T
        C    C        *FIG. 1D*

Probe No.5
AAAAAAAAGA GGGCCTAGGC GC
     GG AT CAT
        T  T
        C  C          *FIG. 1E*

Probe No.6
AAGAAAAAGA GGGCCTAGGC GC
     GG AT CAT
        T  T
        C  C          *FIG. 1F*

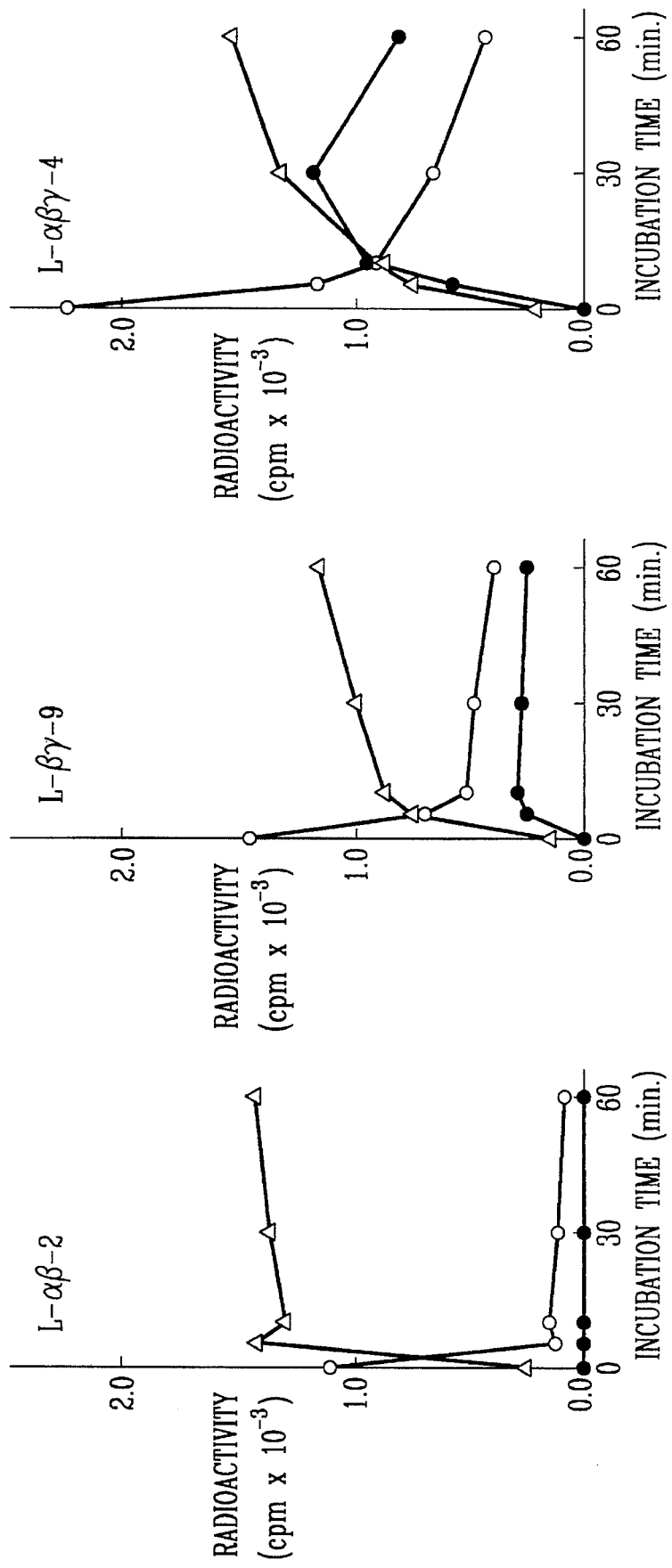

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 1062 base pairs
        ( B ) TYPE: nucleic acid
        ( C ) STRANDEDNESS: unknown
        ( D ) TOPOLOGY: unknown ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:1:

```
GAAGAGCAAG   CGCCATGTTG   AAGCCATCAT   TACCATTCAC   ATCCCTCTTA   TTCCTGCAGC        60

TGCCCCTGCT   GGGAGTGGGG   CTGAACACGA   CAATTCTGAC   GCCCAATGGG   AATGAAGACA       120
```

```
CCACAGCTGA  TTTCTTCCTG  ACCACTATGC  CCACTGACTC  CCTCAGCGTT  TCCACTCTGC   180
CCCTCCCAGA  GGTTCAGTGT  TTTGTGTTCA  ATGTCGAGTA  CATGAATTGC  ACTTGGAACA   240
GCAGCTCTGA  GCCCCAGCCT  ACCAACCTCA  CTCTGCATTA  TTGGTACAAG  AACTCGGATA   300
ATGATAAAGT  CCAGAAGTGC  AGCCACTATC  TATTCTCTGA  AGAAATCACT  TCTGGCTGTC   360
AGTTGCAAAA  AAAGGAGATC  CACCTCTACC  AAACATTTGT  TGTTCAGCTC  CAGGACCCAC   420
GGGAACCCAG  GAGACAGGCC  ACACAGATGC  TAAAACTGCA  GAATCTGGTG  ATCCCTGGG    480
CTCCAGAGAA  CCTAACACTT  CACAAACTGA  GTGAATCCCA  GCTAGAACTG  AACTGGAACA   540
ACAGATTCTT  GAACCACTGT  TTGGAGCACT  TGGTGCAGTA  CCGGACTGAC  TGGGACCACA   600
GCTGGACTGA  ACAATCAGTG  GATTATAGAC  ATAAGTTCTC  CTTGCCTAGT  GTGGATGGGC   660
AGAAACGCTA  CACGTTTCGT  GTTCGGAGCC  GCTTTAACCC  ACTCTGTGGA  AGTGCTCAGC   720
ATTGGAGTGA  ATGGAGCCAC  CCAATCCACT  GGGGGAGCAA  TACTTCAAAA  GAGAATCCTT   780
TCCTGTTTGC  ATTGGAAGCC  GTGGTTATCT  CTGTTGGCTC  CATGGGATTG  ATTATCAGCC   840
TTCTCTGTGT  GTATTTCTGG  CTGGAACGGA  CGATGCCCCG  AATTCCACC   CTGAAGAACC   900
TAGAGGATCT  TGTTACTGAA  TACCACGGGA  ACTTTTCGGC  CTGGAGTGGT  GTGTCTAAGG   960
GACTGGCTGA  GAGTCTGCAG  CCAGACTACA  GTGAACGACT  CTGCCTCGTC  AGTGAGATTC   1020
CCCCAAAAGG  AGGGGCCCTT  GGGGAGGGGC  CTGGGGCCTC  CC                       1062
```

( 2 ) INFORMATION FOR SEQ ID NO:2:

( i ) SEQUENCE CHARACTERISTICS:
        ( A ) LENGTH: 1393 base pairs
        ( B ) TYPE: nucleic acid
        ( C ) STRANDEDNESS: unknown
        ( D ) TOPOLOGY: unknown ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:2:

```
GGGCTGAACA  CGACAATTCT  GACGCCCAAT  GGGAATGAAG  ACACCACAGC  TGATTTCTTC   60
CTGACCACTA  TGCCCACTGA  CTCCCTCAGC  GTTTCCACTC  TGCCCCTCCC  AGAGGTTCAG   120
TGTTTTGTGT  TCAATGTCGA  GTACATGAAT  TGCACTTGGA  ACAGCAGCTC  TGAGCCCCAG   180
CCTACCAACC  TCACTCTGCA  TTATTGGTAC  AAGAACTCGG  ATAATGATAA  AGTCCAGAAG   240
TGCAGCCACT  ATCTATTCTC  TGAAGAAATC  ACTTCTGGCT  GTCAGTTGCA  AAAAAGGAG    300
ATCCACCTCT  ACCAAACATT  TGTTGTTCAG  CTCCAGGACC  CACGGGAACC  CAGGAGACAG   360
GCCACACAGA  TGCTAAAACT  GCAGAATCTG  GTGATCCCCT  GGGCTCCAGA  GAACCTAACA   420
CTTCACAAAC  TGAGTGAATC  CCAGCTAGAA  CTGAACTGGA  ACAACAGATT  CTTGAACCAC   480
TGTTTGGAGC  ACTTGGTGCA  GTACCGGACT  GACTGGGACC  ACAGCTGGAC  TGAACAATCA   540
GTGGATTATA  GACATAAGTT  CTCCTTGCCT  AGTGTGGATG  GGCAGAAACG  CTACACGTTT   600
CGTGTTCGGA  GCCGCTTTAA  CCCACTCTGT  GGAAGTGCTC  AGCATTGGAG  TGAATGGAGC   660
CACCCAATCC  ACTGGGGGAG  CAATACTTCA  AAAGAGAATC  CTTTCCTGTT  TGCATTGGAA   720
GCCGTGGTTA  TCTCTGTTGG  CTCCATGGGA  TTGATTATCA  GCCTTCTCTG  TGTGTATTTC   780
TGGCTGGAAC  GGACGATGCC  CCGAATTCCC  ACCCTGAAGA  ACCTAGAGGA  TCTTGTTACT   840
GAATACCACG  GGAACTTTTC  GGCCTGGAGT  GGTGTGTCTA  AGGGACTGGC  TGAGAGTCTG   900
CAGCCAGACT  ACAGTGAACG  ACTCTGCCTC  GTCAGTGAGA  TTCCCCCAAA  AGGAGGGGCC   960
```

```
CTTGGGGAGG GGCCTGGGGC CTCCCCATGC AACCAGCATA GCCCCTACTG GGCCCCCCCA    1020

TGTTACACCC TAAAGCCTGA AACCTGAACC CCAATCCTCT GACAGAAGAA CCCCAGGGTC    1080

CTGTAGCCCT AAGTGGTACT AACTTTCCTT CATTCAACCC ACCTGCGTCT CATACTCACC    1140

TCACCCCACT GTGGCTGATT TGGAATTTTG TGCCCCCATG TAAGCACCCC TTCATTTGGC    1200

ATTCCCCACT TGAGAATTAC CCTTTTGCCC CGAACATGTT TTCTTCTCC CTCAGTCTGG     1260

CCCTTCCTTT TCGCAGGATT CTTCCTCCCT CCCTCTTTCC CTCCCTTCCT CTTTCCATCT    1320

ACCCTCCGAT TGTTCCTGAA CCGATGAGAA ATAAGTTTC TGTTGATAAT CATCAAAAAA    1380

AAAAAAAAAA AAA                                                       1393
```

( 2 ) INFORMATION FOR SEQ ID NO:3:

( i ) SEQUENCE CHARACTERISTICS:
        ( A ) LENGTH: 1470 base pairs
        ( B ) TYPE: nucleic acid
        ( C ) STRANDEDNESS: unknown
        ( D ) TOPOLOGY: unknown ( i i ) MOLECULE TYPE: cDNA ( v i ) ORIGINAL SOURCE:
        ( A ) ORGANISM: Homo sapiens ( i x ) FEATURE:
        ( A ) NAME/KEY: CDS
        ( B ) LOCATION: 15..1121

( i x ) FEATURE:
        ( A ) NAME/KEY: mat_peptide
        ( B ) LOCATION: 81..1121

( i x ) FEATURE:
        ( A ) NAME/KEY: sig_peptide
        ( B ) LOCATION: 15..80

( x i ) SEQUENCE DESCRIPTION: SEQ ID NO:3:

```
GAAGAGCAAG CGCC ATG TTG AAG CCA TCA TTA CCA TTC ACA TCC CTC TTA               50
               Met Leu Lys Pro Ser Leu Pro Phe Thr Ser Leu Leu
               -22     -20                 -15

TTC CTG CAG CTG CCC CTG CTG GGA GTG GGG CTG AAC ACG ACA ATT CTG               98
Phe Leu Gln Leu Pro Leu Leu Gly Val Gly Leu Asn Thr Thr Ile Leu
-10               -5                   1               5

ACG CCC AAT GGG AAT GAA GAC ACC ACA GCT GAT TTC TTC CTG ACC ACT              146
Thr Pro Asn Gly Asn Glu Asp Thr Thr Ala Asp Phe Phe Leu Thr Thr
            10              15                          20

ATG CCC ACT GAC TCC CTC AGC GTT TCC ACT CTG CCC CTC CCA GAG GTT              194
Met Pro Thr Asp Ser Leu Ser Val Ser Thr Leu Pro Leu Pro Glu Val
        25              30              35

CAG TGT TTT GTG TTC AAT GTC GAG TAC ATG AAT TGC ACT TGG AAC AGC              242
Gln Cys Phe Val Phe Asn Val Glu Tyr Met Asn Cys Thr Trp Asn Ser
    40              45              50

AGC TCT GAG CCC CAG CCT ACC AAC CTC ACT CTG CAT TAT TGG TAC AAG              290
Ser Ser Glu Pro Gln Pro Thr Asn Leu Thr Leu His Tyr Trp Tyr Lys
55              60              65                          70

AAC TCG GAT AAT GAT AAA GTC CAG AAG TGC AGC CAC TAT CTA TTC TCT              338
Asn Ser Asp Asn Asp Lys Val Gln Lys Cys Ser His Tyr Leu Phe Ser
                75              80              85

GAA GAA ATC ACT TCT GGC TGT CAG TTG CAA AAA AAG GAG ATC CAC CTC              386
Glu Glu Ile Thr Ser Gly Cys Gln Leu Gln Lys Lys Glu Ile His Leu
            90              95              100

TAC CAA ACA TTT GTT GTT CAG CTC CAG GAC CCA CGG GAA CCC AGG AGA              434
Tyr Gln Thr Phe Val Val Gln Leu Gln Asp Pro Arg Glu Pro Arg Arg
        105             110             115
```

| | | | | | | | | | | | | | | | | |
|---|---|---|---|---|---|---|---|---|---|---|---|---|---|---|---|---|
| CAG | GCC | ACA | CAG | ATG | CTA | AAA | CTG | CAG | AAT | CTG | GTG | ATC | CCC | TGG | GCT | 482 |
| Gln | Ala | Thr | Gln | Met | Leu | Lys | Leu | Gln | Asn | Leu | Val | Ile | Pro | Trp | Ala | |
| | 120 | | | | 125 | | | | | 130 | | | | | | |
| CCA | GAG | AAC | CTA | ACA | CTT | CAC | AAA | CTG | AGT | GAA | TCC | CAG | CTA | GAA | CTG | 530 |
| Pro | Glu | Asn | Leu | Thr | Leu | His | Lys | Leu | Ser | Glu | Ser | Gln | Leu | Glu | Leu | |
| 135 | | | | | 140 | | | | 145 | | | | | | 150 | |
| AAC | TGG | AAC | AAC | AGA | TTC | TTG | AAC | CAC | TGT | TTG | GAG | CAC | TTG | GTG | CAG | 578 |
| Asn | Trp | Asn | Asn | Arg | Phe | Leu | Asn | His | Cys | Leu | Glu | His | Leu | Val | Gln | |
| | | | | 155 | | | | | 160 | | | | | 165 | | |
| TAC | CGG | ACT | GAC | TGG | GAC | CAC | AGC | TGG | ACT | GAA | CAA | TCA | GTG | GAT | TAT | 626 |
| Tyr | Arg | Thr | Asp | Trp | Asp | His | Ser | Trp | Thr | Glu | Gln | Ser | Val | Asp | Tyr | |
| | | 170 | | | | | 175 | | | | | 180 | | | | |
| AGA | CAT | AAG | TTC | TCC | TTG | CCT | AGT | GTG | GAT | GGG | CAG | AAA | CGC | TAC | ACG | 674 |
| Arg | His | Lys | Phe | Ser | Leu | Pro | Ser | Val | Asp | Gly | Gln | Lys | Arg | Tyr | Thr | |
| | | 185 | | | | | 190 | | | | | 195 | | | | |
| TTT | CGT | GTT | CGG | AGC | CGC | TTT | AAC | CCA | CTC | TGT | GGA | AGT | GCT | CAG | CAT | 722 |
| Phe | Arg | Val | Arg | Ser | Arg | Phe | Asn | Pro | Leu | Cys | Gly | Ser | Ala | Gln | His | |
| | 200 | | | | | 205 | | | | | 210 | | | | | |
| TGG | AGT | GAA | TGG | AGC | CAC | CCA | ATC | CAC | TGG | GGG | AGC | AAT | ACT | TCA | AAA | 770 |
| Trp | Ser | Glu | Trp | Ser | His | Pro | Ile | His | Trp | Gly | Ser | Asn | Thr | Ser | Lys | |
| 215 | | | | | 220 | | | | | 225 | | | | | 230 | |
| GAG | AAT | CCT | TTC | CTG | TTT | GCA | TTG | GAA | GCC | GTG | GTT | ATC | TCT | GTT | GGC | 818 |
| Glu | Asn | Pro | Phe | Leu | Phe | Ala | Leu | Glu | Ala | Val | Val | Ile | Ser | Val | Gly | |
| | | | | 235 | | | | | 240 | | | | | 245 | | |
| TCC | ATG | GGA | TTG | ATT | ATC | AGC | CTT | CTC | TGT | GTG | TAT | TTC | TGG | CTG | GAA | 866 |
| Ser | Met | Gly | Leu | Ile | Ile | Ser | Leu | Leu | Cys | Val | Tyr | Phe | Trp | Leu | Glu | |
| | | 250 | | | | | 255 | | | | | 260 | | | | |
| CGG | ACG | ATG | CCC | CGA | ATT | CCC | ACC | CTG | AAG | AAC | CTA | GAG | GAT | CTT | GTT | 914 |
| Arg | Thr | Met | Pro | Arg | Ile | Pro | Thr | Leu | Lys | Asn | Leu | Glu | Asp | Leu | Val | |
| | | 265 | | | | | 270 | | | | | 275 | | | | |
| ACT | GAA | TAC | CAC | GGG | AAC | TTT | TCG | GCC | TGG | AGT | GGT | GTG | TCT | AAG | GGA | 962 |
| Thr | Glu | Tyr | His | Gly | Asn | Phe | Ser | Ala | Trp | Ser | Gly | Val | Ser | Lys | Gly | |
| | 280 | | | | | 285 | | | | | 290 | | | | | |
| CTG | GCT | GAG | AGT | CTG | CAG | CCA | GAC | TAC | AGT | GAA | CGA | CTC | TGC | CTC | GTC | 1010 |
| Leu | Ala | Glu | Ser | Leu | Gln | Pro | Asp | Tyr | Ser | Glu | Arg | Leu | Cys | Leu | Val | |
| 295 | | | | | 300 | | | | | 305 | | | | | 310 | |
| AGT | GAG | ATT | CCC | CCA | AAA | GGA | GGG | GCC | CTT | GGG | GAG | GGG | CCT | GGG | GCC | 1058 |
| Ser | Glu | Ile | Pro | Pro | Lys | Gly | Gly | Ala | Leu | Gly | Glu | Gly | Pro | Gly | Ala | |
| | | | | 315 | | | | | 320 | | | | | 325 | | |
| TCC | CCA | TGC | AAC | CAG | CAT | AGC | CCC | TAC | TGG | GCC | CCC | CCA | TGT | TAC | ACC | 1106 |
| Ser | Pro | Cys | Asn | Gln | His | Ser | Pro | Tyr | Trp | Ala | Pro | Pro | Cys | Tyr | Thr | |
| | | | 330 | | | | | 335 | | | | | 340 | | | |
| CTA | AAG | CCT | GAA | ACC | TGAACCCCAA | TCCTCTGACA | GAAGAACCCC | AGGGTCCTGT | | | | | | | | 1161 |
| Leu | Lys | Pro | Glu | Thr | | | | | | | | | | | | |
| | | 345 | | | | | | | | | | | | | | |

AGCCCTAAGT GGTACTAACT TTCCTTCATT CAACCCACCT GCGTCTCATA CTCACCTCAC 1221

CCCACTGTGG CTGATTTGGA ATTTTGTGCC CCCATGTAAG CACCCCTTCA TTTGGCATTC 1281

CCCACTTGAG AATTACCCTT TTGCCCCGAA CATGTTTTTC TTCTCCCTCA GTCTGGCCCT 1341

TCCTTTTCGC AGGATTCTTC CTCCCTCCCT CTTTCCCTCC CTTCCTCTTT CCATCTACCC 1401

TCCGATTGTT CCTGAACCGA TGAGAAATAA AGTTTCTGTT GATAATCATC AAAAAAAAA 1461

AAAAAAAA 1470

( 2 ) INFORMATION FOR SEQ ID NO:4:

( i ) SEQUENCE CHARACTERISTICS:
        ( A ) LENGTH: 369 amino acids
        ( B ) TYPE: amino acid
        ( D ) TOPOLOGY: linear (i i) MOLECULE TYPE: protein (x i) SEQUENCE DESCRIPTION: SEQ ID NO:4:

| Met -22 | Leu | Lys -20 | Pro | Ser | Leu | Pro | Phe -15 | Thr | Ser | Leu | Leu | Phe -10 | Leu | Gln | Leu |
|---|---|---|---|---|---|---|---|---|---|---|---|---|---|---|---|
| Pro | Leu -5 | Leu | Gly | Val | Gly 1 | Leu | Asn | Thr | Thr | Ile 5 | Leu | Thr | Pro | Asn | Gly 10 |
| Asn | Glu | Asp | Thr | Thr 15 | Ala | Asp | Phe | Phe | Leu 20 | Thr | Thr | Met | Pro | Thr 25 | Asp |
| Ser | Leu | Ser | Val 30 | Ser | Thr | Leu | Pro | Leu 35 | Pro | Glu | Val | Gln | Cys 40 | Phe | Val |
| Phe | Asn | Val 45 | Glu | Tyr | Met | Asn | Cys 50 | Thr | Trp | Asn | Ser | Ser 55 | Ser | Glu | Pro |
| Gln | Pro 60 | Thr | Asn | Leu | Thr | Leu 65 | His | Tyr | Trp | Tyr | Lys 70 | Asn | Ser | Asp | Asn |
| Asp 75 | Lys | Val | Gln | Lys | Cys 80 | Ser | His | Tyr | Leu | Phe 85 | Ser | Glu | Glu | Ile | Thr 90 |
| Ser | Gly | Cys | Gln | Leu 95 | Gln | Lys | Lys | Glu | Ile 100 | His | Leu | Tyr | Gln | Thr 105 | Phe |
| Val | Val | Gln | Leu 110 | Gln | Asp | Pro | Arg | Glu 115 | Pro | Arg | Arg | Gln | Ala 120 | Thr | Gln |
| Met | Leu | Lys 125 | Leu | Gln | Asn | Leu | Val 130 | Ile | Pro | Trp | Ala | Pro 135 | Glu | Asn | Leu |
| Thr | Leu 140 | His | Lys | Leu | Ser | Glu 145 | Ser | Gln | Leu | Glu | Leu 150 | Asn | Trp | Asn | Asn |
| Arg 155 | Phe | Leu | Asn | His | Cys 160 | Leu | Glu | His | Leu | Val 165 | Gln | Tyr | Arg | Thr | Asp 170 |
| Trp | Asp | His | Ser | Trp 175 | Thr | Glu | Gln | Ser | Val 180 | Asp | Tyr | Arg | His | Lys 185 | Phe |
| Ser | Leu | Pro | Ser 190 | Val | Asp | Gly | Gln | Lys 195 | Arg | Tyr | Thr | Phe | Arg 200 | Val | Arg |
| Ser | Arg | Phe 205 | Asn | Pro | Leu | Cys | Gly 210 | Ser | Ala | Gln | His | Trp 215 | Ser | Glu | Trp |
| Ser | His 220 | Pro | Ile | His | Trp | Gly 225 | Ser | Asn | Thr | Ser | Lys 230 | Glu | Asn | Pro | Phe |
| Leu 235 | Phe | Ala | Leu | Glu | Ala 240 | Val | Val | Ile | Ser | Val 245 | Gly | Ser | Met | Gly | Leu 250 |
| Ile | Ile | Ser | Leu | Leu 255 | Cys | Val | Tyr | Phe | Trp 260 | Leu | Glu | Arg | Thr | Met 265 | Pro |
| Arg | Ile | Pro | Thr 270 | Leu | Lys | Asn | Leu | Glu 275 | Asp | Leu | Val | Thr | Glu 280 | Tyr | His |
| Gly | Asn | Phe 285 | Ser | Ala | Trp | Ser | Gly 290 | Val | Ser | Lys | Gly | Leu 295 | Ala | Glu | Ser |
| Leu | Gln 300 | Pro | Asp | Tyr | Ser | Glu 305 | Arg | Leu | Cys | Leu | Val 310 | Ser | Glu | Ile | Pro |
| Pro 315 | Lys | Gly | Gly | Ala | Leu 320 | Gly | Glu | Gly | Pro | Gly 325 | Ala | Ser | Pro | Cys | Asn 330 |
| Gln | His | Ser | Pro | Tyr 335 | Trp | Ala | Pro | Pro | Cys 340 | Tyr | Thr | Leu | Lys | Pro 345 | Glu |
| Thr | | | | | | | | | | | | | | | |

(2) INFORMATION FOR SEQ ID NO:5:

(i) SEQUENCE CHARACTERISTICS:

(A) LENGTH: 1110 base pairs
(B) TYPE: nucleic acid
(C) STRANDEDNESS: unknown
(D) TOPOLOGY: linear (ii) MOLECULE TYPE: DNA (genomic)

(vi) ORIGINAL SOURCE:
(A) ORGANISM: Homo sapiens (xi) SEQUENCE DESCRIPTION: SEQ ID NO:5:

| | | | | | |
|---|---|---|---|---|---|
| ATGTTGAAGC | CATCATTACC | ATTCACATCC | CTCTTATTCC | TGCAGCTGCC | CCTGCTGGGA | 60 |
| GTGGGGCTGA | ACACGACAAT | TCTGACGCCC | AATGGGAATG | AAGACACCAC | AGCTGATTTC | 120 |
| TTCCTGACCA | CTATGCCCAC | TGACTCCCTC | AGCGTTTCCA | CTCTGCCCCT | CCCAGAGGTT | 180 |
| CAGTGTTTTG | TGTTCAATGT | CGAGTACATG | AATTGCACTT | GGAACAGCAG | CTCTGAGCCC | 240 |
| CAGCCTACCA | ACCTCACTCT | GCATTATTGG | TACAAGAACT | CGGATAATGA | TAAAGTCCAG | 300 |
| AAGTGCAGCC | ACTATCTATT | CTCTGAAGAA | ATCACTTCTG | CTGTCAGTT | GCAAAAAAG | 360 |
| GAGATCCACC | TCTACCAAAC | ATTTGTTGTT | CAGCTCCAGG | ACCCACGGGA | ACCCAGGAGA | 420 |
| CAGGCCACAC | AGATGCTAAA | ACTGCAGAAT | CTGGTGATCC | CCTGGGCTCC | AGAGAACCTA | 480 |
| ACACTTCACA | AACTGAGTGA | ATCCCAGCTA | GAACTGAACT | GGAACAACAG | ATTCTTGAAC | 540 |
| CACTGTTTGG | AGCACTTGGT | GCAGTACCGG | ACTGACTGGG | ACCACAGCTG | GACTGAACAA | 600 |
| TCAGTGGATT | ATAGACATAA | GTTCTCCTTG | CCTAGTGTGG | ATGGGCAGAA | ACGCTACACG | 660 |
| TTTCGTGTTC | GGAGCCGCTT | TAACCCACTC | TGTGGAAGTG | CTCAGCATTG | GAGTGAATGG | 720 |
| AGCCACCCAA | TCCACTGGGG | GAGCAATACT | TCAAAAGAGA | ATCCTTTCCT | GTTTGCATTG | 780 |
| GAAGCCGTGG | TTATCTCTGT | TGGCTCCATG | GGATTGATTA | TCAGCCTTCT | CTGTGTGTAT | 840 |
| TTCTGGCTGG | AACGGACGAT | GCCCCGAATT | CCCACCCTGA | AGAACCTAGA | GGATCTTGTT | 900 |
| ACTGAATACC | ACGGGAACTT | TTCGGCCTGG | AGTGGTGTGT | CTAAGGGACT | GGCTGAGAGT | 960 |
| CTGCAGCCAG | ACTACAGTGA | ACGACTCTGC | CTCGTCAGTG | AGATTCCCCC | AAAAGGAGGG | 1020 |
| GCCCTTGGGG | AGGGGCCTGG | GGCCTCCCCA | TGCAACCAGC | ATAGCCCCTA | CTGGGCCCCC | 1080 |
| CCATGTTACA | CCCTAAAGCC | TGAAACCTGA | | | | 1110 |

(2) INFORMATION FOR SEQ ID NO:6:

(i) SEQUENCE CHARACTERISTICS:
(A) LENGTH: 1044 base pairs
(B) TYPE: nucleic acid
(C) STRANDEDNESS: unknown
(D) TOPOLOGY: linear (ii) MOLECULE TYPE: DNA (genomic)

(vi) ORIGINAL SOURCE:
(A) ORGANISM: Homo sapiens (ix) FEATURE:
(A) NAME/KEY: CDS
(B) LOCATION: 1..1041

(xi) SEQUENCE DESCRIPTION: SEQ ID NO:6:

| CTG | AAC | ACG | ACA | ATT | CTG | ACG | CCC | AAT | GGG | AAT | GAA | GAC | ACC | ACA | GCT | 48 |
|---|---|---|---|---|---|---|---|---|---|---|---|---|---|---|---|---|
| Leu | Asn | Thr | Thr | Ile | Leu | Thr | Pro | Asn | Gly | Asn | Glu | Asp | Thr | Thr | Ala | |
| 1 | | | | 5 | | | | | 10 | | | | | 15 | | |

| GAT | TTC | TTC | CTG | ACC | ACT | ATG | CCC | ACT | GAC | TCC | CTC | AGC | GTT | TCC | ACT | 96 |
|---|---|---|---|---|---|---|---|---|---|---|---|---|---|---|---|---|
| Asp | Phe | Phe | Leu | Thr | Thr | Met | Pro | Thr | Asp | Ser | Leu | Ser | Val | Ser | Thr | |
| | | | 20 | | | | 25 | | | | | 30 | | | | |

| CTG | CCC | CTC | CCA | GAG | GTT | CAG | TGT | TTT | GTG | TTC | AAT | GTC | GAG | TAC | ATG | 144 |
|---|---|---|---|---|---|---|---|---|---|---|---|---|---|---|---|---|
| Leu | Pro | Leu | Pro | Glu | Val | Gln | Cys | Phe | Val | Phe | Asn | Val | Glu | Tyr | Met | |

-continued

```
                35                              40                              45
AAT  TGC  ACT  TGG  AAC  AGC  AGC  TCT  GAG  CCC  CAG  CCT  ACC  AAC  CTC  ACT      192
Asn  Cys  Thr  Trp  Asn  Ser  Ser  Ser  Glu  Pro  Gln  Pro  Thr  Asn  Leu  Thr
          50                        55                        60

CTG  CAT  TAT  TGG  TAC  AAG  AAC  TCG  GAT  AAT  GAT  AAA  GTC  CAG  AAG  TGC      240
Leu  His  Tyr  Trp  Tyr  Lys  Asn  Ser  Asp  Asn  Asp  Lys  Val  Gln  Lys  Cys
65                        70                        75                        80

AGC  CAC  TAT  CTA  TTC  TCT  GAA  GAA  ATC  ACT  TCT  GGC  TGT  CAG  TTG  CAA      288
Ser  His  Tyr  Leu  Phe  Ser  Glu  Glu  Ile  Thr  Ser  Gly  Cys  Gln  Leu  Gln
                         85                        90                        95

AAA  AAG  GAG  ATC  CAC  CTC  TAC  CAA  ACA  TTT  GTT  GTT  CAG  CTC  CAG  GAC      336
Lys  Lys  Glu  Ile  His  Leu  Tyr  Gln  Thr  Phe  Val  Val  Gln  Leu  Gln  Asp
               100                       105                       110

CCA  CGG  GAA  CCC  AGG  AGA  CAG  GCC  ACA  CAG  ATG  CTA  AAA  CTG  CAG  AAT      384
Pro  Arg  Glu  Pro  Arg  Arg  Gln  Ala  Thr  Gln  Met  Leu  Lys  Leu  Gln  Asn
          115                       120                       125

CTG  GTG  ATC  CCC  TGG  GCT  CCA  GAG  AAC  CTA  ACA  CTT  CAC  AAA  CTG  AGT      432
Leu  Val  Ile  Pro  Trp  Ala  Pro  Glu  Asn  Leu  Thr  Leu  His  Lys  Leu  Ser
     130                       135                       140

GAA  TCC  CAG  CTA  GAA  CTG  AAC  TGG  AAC  AAC  AGA  TTC  TTG  AAC  CAC  TGT      480
Glu  Ser  Gln  Leu  Glu  Leu  Asn  Trp  Asn  Asn  Arg  Phe  Leu  Asn  His  Cys
145                       150                       155                       160

TTG  GAG  CAC  TTG  GTG  CAG  TAC  CGG  ACT  GAC  TGG  GAC  CAC  AGC  TGG  ACT      528
Leu  Glu  His  Leu  Val  Gln  Tyr  Arg  Thr  Asp  Trp  Asp  His  Ser  Trp  Thr
                    165                       170                       175

GAA  CAA  TCA  GTG  GAT  TAT  AGA  CAT  AAG  TTC  TCC  TTG  CCT  AGT  GTG  GAT      576
Glu  Gln  Ser  Val  Asp  Tyr  Arg  His  Lys  Phe  Ser  Leu  Pro  Ser  Val  Asp
               180                       185                       190

GGG  CAG  AAA  CGC  TAC  ACG  TTT  CGT  GTT  CGG  AGC  CGC  TTT  AAC  CCA  CTC      624
Gly  Gln  Lys  Arg  Tyr  Thr  Phe  Arg  Val  Arg  Ser  Arg  Phe  Asn  Pro  Leu
          195                       200                       205

TGT  GGA  AGT  GCT  CAG  CAT  TGG  AGT  GAA  TGG  AGC  CAC  CCA  ATC  CAC  TGG      672
Cys  Gly  Ser  Ala  Gln  His  Trp  Ser  Glu  Trp  Ser  His  Pro  Ile  His  Trp
     210                       215                       220

GGG  AGC  AAT  ACT  TCA  AAA  GAG  AAT  CCT  TTC  CTG  TTT  GCA  TTG  GAA  GCC      720
Gly  Ser  Asn  Thr  Ser  Lys  Glu  Asn  Pro  Phe  Leu  Phe  Ala  Leu  Glu  Ala
225                       230                       235                       240

GTG  GTT  ATC  TCT  GTT  GGC  TCC  ATG  GGA  TTG  ATT  ATC  AGC  CTT  CTC  TGT      768
Val  Val  Ile  Ser  Val  Gly  Ser  Met  Gly  Leu  Ile  Ile  Ser  Leu  Leu  Cys
                    245                       250                       255

GTG  TAT  TTC  TGG  CTG  GAA  CGG  ACG  ATG  CCC  CGA  ATT  CCC  ACC  CTG  AAG      816
Val  Tyr  Phe  Trp  Leu  Glu  Arg  Thr  Met  Pro  Arg  Ile  Pro  Thr  Leu  Lys
               260                       265                       270

AAC  CTA  GAG  GAT  CTT  GTT  ACT  GAA  TAC  CAC  GGG  AAC  TTT  TCG  GCC  TGG      864
Asn  Leu  Glu  Asp  Leu  Val  Thr  Glu  Tyr  His  Gly  Asn  Phe  Ser  Ala  Trp
          275                       280                       285

AGT  GGT  GTG  TCT  AAG  GGA  CTG  GCT  GAG  AGT  CTG  CAG  CCA  GAC  TAC  AGT      912
Ser  Gly  Val  Ser  Lys  Gly  Leu  Ala  Glu  Ser  Leu  Gln  Pro  Asp  Tyr  Ser
     290                       295                       300

GAA  CGA  CTC  TGC  CTC  GTC  AGT  GAG  ATT  CCC  CCA  AAA  GGA  GGG  GCC  CTT      960
Glu  Arg  Leu  Cys  Leu  Val  Ser  Glu  Ile  Pro  Pro  Lys  Gly  Gly  Ala  Leu
305                       310                       315                       320

GGG  GAG  GGG  CCT  GGG  GCC  TCC  CCA  TGC  AAC  CAG  CAT  AGC  CCC  TAC  TGG     1008
Gly  Glu  Gly  Pro  Gly  Ala  Ser  Pro  Cys  Asn  Gln  His  Ser  Pro  Tyr  Trp
                    325                       330                       335

GCC  CCC  CCA  TGT  TAC  ACC  CTA  AAG  CCT  GAA  ACC  TGA                         1044
Ala  Pro  Pro  Cys  Tyr  Thr  Leu  Lys  Pro  Glu  Thr
               340                       345
```

( 2 ) INFORMATION FOR SEQ ID NO:7:

( i ) SEQUENCE CHARACTERISTICS:
    ( A ) LENGTH: 347 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

```
Leu Asn Thr Thr Ile Leu Thr Pro Asn Gly Asn Glu Asp Thr Thr Ala
  1               5                  10                  15

Asp Phe Phe Leu Thr Thr Met Pro Thr Asp Ser Leu Ser Val Ser Thr
             20                  25                  30

Leu Pro Leu Pro Glu Val Gln Cys Phe Val Phe Asn Val Glu Tyr Met
             35                  40                  45

Asn Cys Thr Trp Asn Ser Ser Ser Glu Pro Gln Pro Thr Asn Leu Thr
     50                  55                  60

Leu His Tyr Trp Tyr Lys Asn Ser Asp Asn Asp Lys Val Gln Lys Cys
 65                  70                  75                  80

Ser His Tyr Leu Phe Ser Glu Glu Ile Thr Ser Gly Cys Gln Leu Gln
                 85                  90                  95

Lys Lys Glu Ile His Leu Tyr Gln Thr Phe Val Val Gln Leu Gln Asp
             100                 105                 110

Pro Arg Glu Pro Arg Arg Gln Ala Thr Gln Met Leu Lys Leu Gln Asn
             115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
                180                 185                 190

Gly Gln Lys Arg Tyr Thr Phe Arg Val Arg Ser Arg Phe Asn Pro Leu
            195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

Val Val Ile Ser Val Gly Ser Met Gly Leu Ile Ile Ser Leu Leu Cys
                245                 250                 255

Val Tyr Phe Trp Leu Glu Arg Thr Met Pro Arg Ile Pro Thr Leu Lys
            260                 265                 270

Asn Leu Glu Asp Leu Val Thr Glu Tyr His Gly Asn Phe Ser Ala Trp
        275                 280                 285

Ser Gly Val Ser Lys Gly Leu Ala Glu Ser Leu Gln Pro Asp Tyr Ser
    290                 295                 300

Glu Arg Leu Cys Leu Val Ser Glu Ile Pro Pro Lys Gly Gly Ala Leu
305                 310                 315                 320

Gly Glu Gly Pro Gly Ala Ser Pro Cys Asn Gln His Ser Pro Tyr Trp
            325                 330                 335

Ala Pro Pro Cys Tyr Thr Leu Lys Pro Glu Thr
            340                 345
```

( 2 ) INFORMATION FOR SEQ ID NO:8:

( i ) SEQUENCE CHARACTERISTICS:

( A ) LENGTH: 759 base pairs
( B ) TYPE: nucleic acid
( C ) STRANDEDNESS: unknown
( D ) TOPOLOGY: linear ( i i ) MOLECULE TYPE: DNA (genomic)

( v i ) ORIGINAL SOURCE:
( A ) ORGANISM: Homo sapiens ( i x ) FEATURE:
( A ) NAME/KEY: CDS
( B ) LOCATION: 1..756

( i x ) FEATURE:
( A ) NAME/KEY: sig_peptide
( B ) LOCATION: 1..66

( i x ) FEATURE:
( A ) NAME/KEY: mat_peptide
( B ) LOCATION: 67..756

( x i ) SEQUENCE DESCRIPTION: SEQ ID NO:8:

| ATG | TTG | AAG | CCA | TCA | TTA | CCA | TTC | ACA | TCC | CTC | TTA | TTC | CTG | CAG | CTG | 48 |
| Met | Leu | Lys | Pro | Ser | Leu | Pro | Phe | Thr | Ser | Leu | Leu | Phe | Leu | Gln | Leu | |
| -22 | | -20 | | | | | -15 | | | | | | -10 | | | |
| CCC | CTG | CTG | GGA | GTG | GGG | CTG | AAC | ACG | ACA | ATT | CTG | ACG | CCC | AAT | GGG | 96 |
| Pro | Leu | Leu | Gly | Val | Gly | Leu | Asn | Thr | Thr | Ile | Leu | Thr | Pro | Asn | Gly | |
| | -5 | | | | | 1 | | | | 5 | | | | | 10 | |
| AAT | GAA | GAC | ACC | ACA | GCT | GAT | TTC | TTC | CTG | ACC | ACT | ATG | CCC | ACT | GAC | 144 |
| Asn | Glu | Asp | Thr | Thr | Ala | Asp | Phe | Phe | Leu | Thr | Thr | Met | Pro | Thr | Asp | |
| | | | | 15 | | | | | 20 | | | | | 25 | | |
| TCC | CTC | AGC | GTT | TCC | ACT | CTG | CCC | CTC | CCA | GAG | GTT | CAG | TGT | TTT | GTG | 192 |
| Ser | Leu | Ser | Val | Ser | Thr | Leu | Pro | Leu | Pro | Glu | Val | Gln | Cys | Phe | Val | |
| | | | 30 | | | | | 35 | | | | | 40 | | | |
| TTC | AAT | GTC | GAG | TAC | ATG | AAT | TGC | ACT | TGG | AAC | AGC | AGC | TCT | GAG | CCC | 240 |
| Phe | Asn | Val | Glu | Tyr | Met | Asn | Cys | Thr | Trp | Asn | Ser | Ser | Ser | Glu | Pro | |
| | | 45 | | | | | 50 | | | | | 55 | | | | |
| CAG | CCT | ACC | AAC | CTC | ACT | CTG | CAT | TAT | TGG | TAC | AAG | AAC | TCG | GAT | AAT | 288 |
| Gln | Pro | Thr | Asn | Leu | Thr | Leu | His | Tyr | Trp | Tyr | Lys | Asn | Ser | Asp | Asn | |
| | 60 | | | | | 65 | | | | | 70 | | | | | |
| GAT | AAA | GTC | CAG | AAG | TGC | AGC | CAC | TAT | CTA | TTC | TCT | GAA | GAA | ATC | ACT | 336 |
| Asp | Lys | Val | Gln | Lys | Cys | Ser | His | Tyr | Leu | Phe | Ser | Glu | Glu | Ile | Thr | |
| 75 | | | | | 80 | | | | | 85 | | | | | 90 | |
| TCT | GGC | TGT | CAG | TTG | CAA | AAA | AAG | GAG | ATC | CAC | CTC | TAC | CAA | ACA | TTT | 384 |
| Ser | Gly | Cys | Gln | Leu | Gln | Lys | Lys | Glu | Ile | His | Leu | Tyr | Gln | Thr | Phe | |
| | | | | 95 | | | | | 100 | | | | | 105 | | |
| GTT | GTT | CAG | CTC | CAG | GAC | CCA | CGG | GAA | CCC | AGG | AGA | CAG | GCC | ACA | CAG | 432 |
| Val | Val | Gln | Leu | Gln | Asp | Pro | Arg | Glu | Pro | Arg | Arg | Gln | Ala | Thr | Gln | |
| | | | 110 | | | | | 115 | | | | | 120 | | | |
| ATG | CTA | AAA | CTG | CAG | AAT | CTG | GTG | ATC | CCC | TGG | GCT | CCA | GAG | AAC | CTA | 480 |
| Met | Leu | Lys | Leu | Gln | Asn | Leu | Val | Ile | Pro | Trp | Ala | Pro | Glu | Asn | Leu | |
| | | 125 | | | | | 130 | | | | | 135 | | | | |
| ACA | CTT | CAC | AAA | CTG | AGT | GAA | TCC | CAG | CTA | GAA | CTG | AAC | TGG | AAC | AAC | 528 |
| Thr | Leu | His | Lys | Leu | Ser | Glu | Ser | Gln | Leu | Glu | Leu | Asn | Trp | Asn | Asn | |
| | 140 | | | | | 145 | | | | | 150 | | | | | |
| AGA | TTC | TTG | AAC | CAC | TGT | TTG | GAG | CAC | TTG | GTG | CAG | TAC | CGG | ACT | GAC | 576 |
| Arg | Phe | Leu | Asn | His | Cys | Leu | Glu | His | Leu | Val | Gln | Tyr | Arg | Thr | Asp | |
| 155 | | | | | 160 | | | | | 165 | | | | | 170 | |
| TGG | GAC | CAC | AGC | TGG | ACT | GAA | CAA | TCA | GTG | GAT | TAT | AGA | CAT | AAG | TTC | 624 |
| Trp | Asp | His | Ser | Trp | Thr | Glu | Gln | Ser | Val | Asp | Tyr | Arg | His | Lys | Phe | |
| | | | | 175 | | | | | 180 | | | | | 185 | | |
| TCC | TTG | CCT | AGT | GTG | GAT | GGG | CAG | AAA | CGC | TAC | ACG | TTT | CGT | GTT | CGG | 672 |
| Ser | Leu | Pro | Ser | Val | Asp | Gly | Gln | Lys | Arg | Tyr | Thr | Phe | Arg | Val | Arg | |
| | | | 190 | | | | | 195 | | | | | 200 | | | |

| AGC | CGC | TTT | AAC | CCA | CTC | TGT | GGA | AGT | GCT | CAG | CAT | TGG | AGT | GAA | TGG | 720 |
|---|---|---|---|---|---|---|---|---|---|---|---|---|---|---|---|---|
| Ser | Arg | Phe | Asn | Pro | Leu | Cys | Gly | Ser | Ala | Gln | His | Trp | Ser | Glu | Trp | |
| | | 205 | | | | 210 | | | | | | 215 | | | | |

| AGC | CAC | CCA | ATC | CAC | TGG | GGG | AGC | AAT | ACT | TCA | AAA | TAG | | | | 759 |
|---|---|---|---|---|---|---|---|---|---|---|---|---|---|---|---|---|
| Ser | His | Pro | Ile | His | Trp | Gly | Ser | Asn | Thr | Ser | Lys | | | | | |
| | 220 | | | | 225 | | | | | 230 | | | | | | |

( 2 ) INFORMATION FOR SEQ ID NO:9:

( i ) SEQUENCE CHARACTERISTICS:
( A ) LENGTH: 252 amino acids
( B ) TYPE: amino acid
( D ) TOPOLOGY: linear ( i i ) MOLECULE TYPE: protein ( x i ) SEQUENCE DESCRIPTION: SEQ ID NO:9:

| Met | Leu | Lys | Pro | Ser | Leu | Pro | Phe | Thr | Ser | Leu | Leu | Phe | Leu | Gln | Leu |
|---|---|---|---|---|---|---|---|---|---|---|---|---|---|---|---|
| -22 | | -20 | | | | | -15 | | | | | -10 | | | |

| Pro | Leu | Leu | Gly | Val | Gly | Leu | Asn | Thr | Thr | Ile | Leu | Thr | Pro | Asn | Gly |
|---|---|---|---|---|---|---|---|---|---|---|---|---|---|---|---|
| | | -5 | | | | 1 | | | | 5 | | | | | 10 |

| Asn | Glu | Asp | Thr | Thr | Ala | Asp | Phe | Phe | Leu | Thr | Thr | Met | Pro | Thr | Asp |
|---|---|---|---|---|---|---|---|---|---|---|---|---|---|---|---|
| | | | | 15 | | | | | 20 | | | | | 25 | |

| Ser | Leu | Ser | Val | Ser | Thr | Leu | Pro | Leu | Pro | Glu | Val | Gln | Cys | Phe | Val |
|---|---|---|---|---|---|---|---|---|---|---|---|---|---|---|---|
| | | | 30 | | | | | 35 | | | | | 40 | | |

| Phe | Asn | Val | Glu | Tyr | Met | Asn | Cys | Thr | Trp | Asn | Ser | Ser | Ser | Glu | Pro |
|---|---|---|---|---|---|---|---|---|---|---|---|---|---|---|---|
| | | 45 | | | | | 50 | | | | | 55 | | | |

| Gln | Pro | Thr | Asn | Leu | Thr | Leu | His | Tyr | Trp | Tyr | Lys | Asn | Ser | Asp | Asn |
|---|---|---|---|---|---|---|---|---|---|---|---|---|---|---|---|
| | 60 | | | | | 65 | | | | | 70 | | | | |

| Asp | Lys | Val | Gln | Lys | Cys | Ser | His | Tyr | Leu | Phe | Ser | Glu | Glu | Ile | Thr |
|---|---|---|---|---|---|---|---|---|---|---|---|---|---|---|---|
| 75 | | | | | 80 | | | | | 85 | | | | | 90 |

| Ser | Gly | Cys | Gln | Leu | Gln | Lys | Lys | Glu | Ile | His | Leu | Tyr | Gln | Thr | Phe |
|---|---|---|---|---|---|---|---|---|---|---|---|---|---|---|---|
| | | | | 95 | | | | | 100 | | | | | 105 | |

| Val | Val | Gln | Leu | Gln | Asp | Pro | Arg | Glu | Pro | Arg | Arg | Gln | Ala | Thr | Gln |
|---|---|---|---|---|---|---|---|---|---|---|---|---|---|---|---|
| | | | 110 | | | | | 115 | | | | | 120 | | |

| Met | Leu | Lys | Leu | Gln | Asn | Leu | Val | Ile | Pro | Trp | Ala | Pro | Glu | Asn | Leu |
|---|---|---|---|---|---|---|---|---|---|---|---|---|---|---|---|
| | | 125 | | | | | 130 | | | | | 135 | | | |

| Thr | Leu | His | Lys | Leu | Ser | Glu | Ser | Gln | Leu | Glu | Leu | Asn | Trp | Asn | Asn |
|---|---|---|---|---|---|---|---|---|---|---|---|---|---|---|---|
| | 140 | | | | | 145 | | | | | 150 | | | | |

| Arg | Phe | Leu | Asn | His | Cys | Leu | Glu | His | Leu | Val | Gln | Tyr | Arg | Thr | Asp |
|---|---|---|---|---|---|---|---|---|---|---|---|---|---|---|---|
| 155 | | | | | 160 | | | | | 165 | | | | | 170 |

| Trp | Asp | His | Ser | Trp | Thr | Glu | Gln | Ser | Val | Asp | Tyr | Arg | His | Lys | Phe |
|---|---|---|---|---|---|---|---|---|---|---|---|---|---|---|---|
| | | | | 175 | | | | | 180 | | | | | 185 | |

| Ser | Leu | Pro | Ser | Val | Asp | Gly | Gln | Lys | Arg | Tyr | Thr | Phe | Arg | Val | Arg |
|---|---|---|---|---|---|---|---|---|---|---|---|---|---|---|---|
| | | | 190 | | | | | 195 | | | | | 200 | | |

| Ser | Arg | Phe | Asn | Pro | Leu | Cys | Gly | Ser | Ala | Gln | His | Trp | Ser | Glu | Trp |
|---|---|---|---|---|---|---|---|---|---|---|---|---|---|---|---|
| | | 205 | | | | | 210 | | | | | 215 | | | |

| Ser | His | Pro | Ile | His | Trp | Gly | Ser | Asn | Thr | Ser | Lys | | | | |
|---|---|---|---|---|---|---|---|---|---|---|---|---|---|---|---|
| | 220 | | | | 225 | | | | | 230 | | | | | |

( 2 ) INFORMATION FOR SEQ ID NO:10:

( i ) SEQUENCE CHARACTERISTICS:
( A ) LENGTH: 693 base pairs
( B ) TYPE: nucleic acid
( C ) STRANDEDNESS: unknown
( D ) TOPOLOGY: linear ( i i ) MOLECULE TYPE: DNA (genomic)

( v i ) ORIGINAL SOURCE:

(A) ORGANISM: Homo sapiens (ix) FEATURE:
    (A) NAME/KEY: CDS
    (B) LOCATION: 1..690

(xi) SEQUENCE DESCRIPTION: SEQ ID NO:10:

```
CTG AAC ACG ACA ATT CTG ACG CCC AAT GGG AAT GAA GAC ACC ACA GCT        48
Leu Asn Thr Thr Ile Leu Thr Pro Asn Gly Asn Glu Asp Thr Thr Ala
  1               5                  10                  15

GAT TTC TTC CTG ACC ACT ATG CCC ACT GAC TCC CTC AGC GTT TCC ACT        96
Asp Phe Phe Leu Thr Thr Met Pro Thr Asp Ser Leu Ser Val Ser Thr
             20                  25                  30

CTG CCC CTC CCA GAG GTT CAG TGT TTT GTG TTC AAT GTC GAG TAC ATG       144
Leu Pro Leu Pro Glu Val Gln Cys Phe Val Phe Asn Val Glu Tyr Met
         35                  40                  45

AAT TGC ACT TGG AAC AGC AGC TCT GAG CCC CAG CCT ACC AAC CTC ACT       192
Asn Cys Thr Trp Asn Ser Ser Ser Glu Pro Gln Pro Thr Asn Leu Thr
     50                  55                  60

CTG CAT TAT TGG TAC AAG AAC TCG GAT AAT GAT AAA GTC CAG AAG TGC       240
Leu His Tyr Trp Tyr Lys Asn Ser Asp Asn Asp Lys Val Gln Lys Cys
 65                  70                  75                  80

AGC CAC TAT CTA TTC TCT GAA GAA ATC ACT TCT GGC TGT CAG TTG CAA       288
Ser His Tyr Leu Phe Ser Glu Glu Ile Thr Ser Gly Cys Gln Leu Gln
                 85                  90                  95

AAA AAG GAG ATC CAC CTC TAC CAA ACA TTT GTT GTT CAG CTC CAG GAC       336
Lys Lys Glu Ile His Leu Tyr Gln Thr Phe Val Val Gln Leu Gln Asp
            100                 105                 110

CCA CGG GAA CCC AGG AGA CAG GCC ACA CAG ATG CTA AAA CTG CAG AAT       384
Pro Arg Glu Pro Arg Arg Gln Ala Thr Gln Met Leu Lys Leu Gln Asn
        115                 120                 125

CTG GTG ATC CCC TGG GCT CCA GAG AAC CTA ACA CTT CAC AAA CTG AGT       432
Leu Val Ile Pro Trp Ala Pro Glu Asn Leu Thr Leu His Lys Leu Ser
    130                 135                 140

GAA TCC CAG CTA GAA CTG AAC TGG AAC AAC AGA TTC TTG AAC CAC TGT       480
Glu Ser Gln Leu Glu Leu Asn Trp Asn Asn Arg Phe Leu Asn His Cys
145                 150                 155                 160

TTG GAG CAC TTG GTG CAG TAC CGG ACT GAC TGG GAC CAC AGC TGG ACT       528
Leu Glu His Leu Val Gln Tyr Arg Thr Asp Trp Asp His Ser Trp Thr
                165                 170                 175

GAA CAA TCA GTG GAT TAT AGA CAT AAG TTC TCC TTG CCT AGT GTG GAT       576
Glu Gln Ser Val Asp Tyr Arg His Lys Phe Ser Leu Pro Ser Val Asp
            180                 185                 190

GGG CAG AAA CGC TAC ACG TTT CGT GTT CGG AGC CGC TTT AAC CCA CTC       624
Gly Gln Lys Arg Tyr Thr Phe Arg Val Arg Ser Arg Phe Asn Pro Leu
        195                 200                 205

TGT GGA AGT GCT CAG CAT TGG AGT GAA TGG AGC CAC CCA ATC CAC TGG       672
Cys Gly Ser Ala Gln His Trp Ser Glu Trp Ser His Pro Ile His Trp
    210                 215                 220

GGG AGC AAT ACT TCA AAA TAG                                           693
Gly Ser Asn Thr Ser Lys
225                 230
```

(2) INFORMATION FOR SEQ ID NO:11:

(i) SEQUENCE CHARACTERISTICS:
        (A) LENGTH: 230 amino acids
        (B) TYPE: amino acid
        (D) TOPOLOGY: linear (ii) MOLECULE TYPE: protein (xi) SEQUENCE DESCRIPTION: SEQ ID NO:11:

| | | | | | | | | | | | | | | |
|---|---|---|---|---|---|---|---|---|---|---|---|---|---|---|
| Leu | Asn | Thr | Thr | Ile | Leu | Thr | Pro | Asn | Gly | Asn | Glu | Asp | Thr | Thr | Ala |
| 1 | | | | 5 | | | | | 10 | | | | | 15 | |
| Asp | Phe | Phe | Leu | Thr | Thr | Met | Pro | Thr | Asp | Ser | Leu | Ser | Val | Ser | Thr |
| | | | 20 | | | | 25 | | | | | 30 | | | |
| Leu | Pro | Leu | Pro | Glu | Val | Gln | Cys | Phe | Val | Phe | Asn | Val | Glu | Tyr | Met |
| | | 35 | | | | | 40 | | | | | 45 | | | |
| Asn | Cys | Thr | Trp | Asn | Ser | Ser | Ser | Glu | Pro | Gln | Pro | Thr | Asn | Leu | Thr |
| 50 | | | | | 55 | | | | | 60 | | | | | |
| Leu | His | Tyr | Trp | Tyr | Lys | Asn | Ser | Asp | Asn | Asp | Lys | Val | Gln | Lys | Cys |
| 65 | | | | | 70 | | | | 75 | | | | | | 80 |
| Ser | His | Tyr | Leu | Phe | Ser | Glu | Glu | Ile | Thr | Ser | Gly | Cys | Gln | Leu | Gln |
| | | | | 85 | | | | | 90 | | | | | 95 | |
| Lys | Lys | Glu | Ile | His | Leu | Tyr | Gln | Thr | Phe | Val | Val | Gln | Leu | Gln | Asp |
| | | | 100 | | | | | 105 | | | | | 110 | | |
| Pro | Arg | Glu | Pro | Arg | Arg | Gln | Ala | Thr | Gln | Met | Leu | Lys | Leu | Gln | Asn |
| | | 115 | | | | | 120 | | | | | 125 | | | |
| Leu | Val | Ile | Pro | Trp | Ala | Pro | Glu | Asn | Leu | Thr | Leu | His | Lys | Leu | Ser |
| | 130 | | | | 135 | | | | | 140 | | | | | |
| Glu | Ser | Gln | Leu | Glu | Leu | Asn | Trp | Asn | Asn | Arg | Phe | Leu | Asn | His | Cys |
| 145 | | | | | 150 | | | | | 155 | | | | | 160 |
| Leu | Glu | His | Leu | Val | Gln | Tyr | Arg | Thr | Asp | Trp | Asp | His | Ser | Trp | Thr |
| | | | | 165 | | | | | 170 | | | | | 175 | |
| Glu | Gln | Ser | Val | Asp | Tyr | Arg | His | Lys | Phe | Ser | Leu | Pro | Ser | Val | Asp |
| | | | 180 | | | | | 185 | | | | | 190 | | |
| Gly | Gln | Lys | Arg | Tyr | Thr | Phe | Arg | Val | Arg | Ser | Arg | Phe | Asn | Pro | Leu |
| | | | 195 | | | | | 200 | | | | | 205 | | |
| Cys | Gly | Ser | Ala | Gln | His | Trp | Ser | Glu | Trp | Ser | His | Pro | Ile | His | Trp |
| | 210 | | | | | 215 | | | | | 220 | | | | |
| Gly | Ser | Asn | Thr | Ser | Lys | | | | | | | | | | |
| 225 | | | | | 230 | | | | | | | | | | |

( 2 ) INFORMATION FOR SEQ ID NO:12:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:12:

| | | | | | | | | | | | | | | |
|---|---|---|---|---|---|---|---|---|---|---|---|---|---|---|
| Leu | Asn | Thr | Thr | Ile | Leu | Thr | Pro | Asn | Gly | Asn | Glu | Asp | Thr | Thr | Ala |
| 1 | | | | 5 | | | | | 10 | | | | | 15 | |
| Asp | Phe | Phe | Leu | | | | | | | | | | | | |
| | | | 20 | | | | | | | | | | | | |

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:13:

ATHYTRACNC CNAATGG 17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:14:

ATHYTRACNC CNAACGG 17

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:15:

ATHCTYACNC CNAATGG 17

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:16:

ATHCTYACNC CDMATGG 17

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:17:

AAAAARRANW SNKCCTAGGC GC 22

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: unknown
        (D) TOPOLOGY: linear (ii) MOLECULE TYPE: DNA (genomic)

(xi) SEQUENCE DESCRIPTION: SEQ ID NO:18:

AAGAARRANW SNKCCTAGGC GC 22

(2) INFORMATION FOR SEQ ID NO:19:

( i ) SEQUENCE CHARACTERISTICS:
  ( A ) LENGTH: 20 amino acids
  ( B ) TYPE: amino acid
  ( D ) TOPOLOGY: linear ( i i ) MOLECULE TYPE: peptide ( v ) FRAGMENT TYPE: N-terminal ( v i ) ORIGINAL SOURCE:
  ( A ) ORGANISM: Homo sapiens ( i x ) FEATURE:
  ( A ) NAME/KEY: Modified-site
  ( B ) LOCATION: 1..2
  ( D ) OTHER INFORMATION: /note="Leu or Ile"

( i x ) FEATURE:
  ( A ) NAME/KEY: Modified-site
  ( B ) LOCATION: 2..3
  ( D ) OTHER INFORMATION: /note="Asn or Cys"

( i x ) FEATURE:
  ( A ) NAME/KEY: Modified-site
  ( B ) LOCATION: 3..4
  ( D ) OTHER INFORMATION: /note="Thr or Phe"

( i x ) FEATURE:
  ( A ) NAME/KEY: Modified-site
  ( B ) LOCATION: 4..5
  ( D ) OTHER INFORMATION: /note="Thr or Phe"

( i x ) FEATURE:
  ( A ) NAME/KEY: Modified-site
  ( B ) LOCATION: 13..14
  ( D ) OTHER INFORMATION: /note="Asp or Arg"

( i x ) FEATURE:
  ( A ) NAME/KEY: Modified-site
  ( B ) LOCATION: 14..15
  ( D ) OTHER INFORMATION: /note="Thr or Ala"

( i x ) FEATURE:
  ( A ) NAME/KEY: Modified-site
  ( B ) LOCATION: 17..18
  ( D ) OTHER INFORMATION: /note="Asp or Gly"

( x i ) SEQUENCE DESCRIPTION: SEQ ID NO:19:

Xaa  Xaa  Xaa  Xaa  Ile  Leu  Thr  Pro  Asn  Gly  Asn  Glu  Xaa  Xaa  Xaa  Ala
1                  5                        10                       15

Xaa  Phe  Phe  Leu
          20

( 2 ) INFORMATION FOR SEQ ID NO:20:

( i ) SEQUENCE CHARACTERISTICS:
    ( A ) LENGTH: 26 base pairs
    ( B ) TYPE: nucleic acid
    ( C ) STRANDEDNESS: unknown
    ( D ) TOPOLOGY: linear ( i i ) MOLECULE TYPE: DNA (genomic)

( x i ) SEQUENCE DESCRIPTION: SEQ ID NO:20:

AGCTCGAGCG CCATGTTGAA GCCCAT                               26

( 2 ) INFORMATION FOR SEQ ID NO:21:

( i ) SEQUENCE CHARACTERISTICS:
    ( A ) LENGTH: 28 base pairs
    ( B ) TYPE: nucleic acid
    ( C ) STRANDEDNESS: unknown
    ( D ) TOPOLOGY: linear ( i i ) MOLECULE TYPE: DNA (genomic)

( x i ) SEQUENCE DESCRIPTION: SEQ ID NO:21:

AACTCGAGAG GATTCTATTT TGAAGTAT                                                                 2 8

HUMAN IL-2 RECEPTOR γ CHAIN MOLECULE

The present invention relates to an IL-2 receptor γ chain molecule which directs the transduction of signals from IL-2, an IL-2 receptor γ chain molecule of human origin, a DNA sequence encoding an IL-2 receptor γ chain molecule, particularly the human IL-2 receptor γ chain molecule, a vector including one of said DNA sequences, a cell transformed with said vector, a method for the production of an IL-2 receptor γ chain molecule, particularly of human origin, by culturing said cell, an immune response regulatory agent comprising an IL-2 receptor γ chain molecule, especially the human IL-2 receptor γ chain molecule, a method for the detection or assay of the gene encoding an IL-2 receptor γ chain molecule, particularly the human IL-2 receptor γ chain molecule, an antibody capable of binding to an IL-2 receptor γ chain molecule, an antibody capable of binding to the human IL-2 receptor γ chain molecule, an immune response regulatory agent comprising said antibody, and a method for detection or assay of an IL-2 receptor γ chain molecule, particularly the human IL-2 receptor γ chain molecule, by use of said antibody. The existence of the present human IL-2 receptor γ chain molecule became known for the first time by the present invention. It is a substance useful for the clarification of IL-2/IL-2 receptor system and the development of a method for therapy or diagnosis of diseases due to immunopathy.

DESCRIPTION OF THE PRIOR ART

IL-2 is a protein produced by helper T-cells, which is a very important factor for biophylaxis, and is known to be involved in growth and differentiation induction of killer T-cells and to act on a variety of immunocompetenT-cells including B cells, macrophages, natural killer (NK) cells and lymphokine-activated killer (LAK) cells in the body (Science, 240, p. 1169, 1988). Diseases known generically as autoimmune diseases are charac-terized by an attack of auto antibodies on self-components or by an attack of T-cells which attack the self, and most of them are known to be intractable ones of unknown etiology. For not a few of these autoimmune diseases, excessive or disordered production of IL-2 is considered to be one of the main factors causing aggravation of the condition.

In addition, prevention of the rejection of a transplant is understood to lead to success in organ transplantation, and the main mechanism of rejection is presumed to be the attack on the transplant by killer T-cells which have been activated by IL-2 (Transplantation Proceedings, 15, p. 264, 1983).

Incidentally, the physiological activity of IL-2 is known to be exerted through a receptor on the surface of effector cells which combines with IL-2 specifically. In the past, the IL-2 receptor present on activated T-cells was thought to include three types of different binding affinities for IL-2, i.e. high affinitive binding ($Kd=10^{11}/M$), intermediate affinitive binding ($Kd=10^9/M$) and low affinitive binding ($Kd=10^8/M$).

In 1984 a gene for a receptor molecule of 55 kd was isolated which is now called the α chain (Nature, 311, p. 626, 1984; and Nature, 311, p. 631, 1984). A genetic experiment for transfection of the cDNA for the present receptor into a eucaryocyte revealed that the α chain can be a low affinity receptor by itself, and that it is a molecule required for the formation of a functional high affinity receptor (Nature, 318, p. 467, 1985; Journal of Experimental Medicine, 162, p. 363, 1986; and Nature, 320, p. 75, 1986). However, because of the lack of the signal transduction region in the isolated α chain cDNA, another molecule has been believed to exist which is involved in the formation of a high affinity receptor and in the signal transduction.

Thereafter another gene for a receptor molecule of 75 kd was isolated, which is now called the β chain (Science, 244, p. 551, 1989), and the experiment for transfection of the gene into lymphoid cells confirmed that a functional intermediate affinitive receptor is formed only with the β chain, and that simultaneous transfection of the genes for α and β chains produces a functional high affinity receptor. These results have led us to the conclusions that a low affinity receptor consists of the α chain only, whereas an intermediate affinity receptor consists only of the β chain, that association of α and β chains through a noncovalent binding forms a high affinity receptor, and that the signal transduction occurs only when both intermediate and high affinity receptors are combined.

The structure of the β chain estimated on the basis of the sequence of the cDNA for the β chain of the IL-2 receptor includes a cytoplasmic region of 286 amino acid residues which is large enough to bear the signal transduction, but, nevertheless, no amino acid sequence homology was found which suggests a structural correlationship with known signal transduction molecules, such as tyrosine kinase. In addition, no binding to IL-2 occurred in the experiment for the gene transfection in the case where fibroblasts, i.e. nonlymphoid cells, were used instead of lymphoid cells (Science, 244, p. 551, 1989). Simultaneous transfection of the genes for the α and β chains certainly succeeded in the formation of a high affinity receptor in the same manner as in the case where a lymphoid cell was used, but was unsuccessful in internalising the IL-2 signal and forming a receptor with complete function (Journal of Immunology, 145, p. 2177, 1990).

These facts suggest the necessity of somewhat modifying the β chain itself or of the presence of a molecule other than α and β chains which has some interactions with the β chain, in order that the β chain acquires ability to bind to IL-2 by itself, acquires ability of signal transduction and for the formation of a functional, complete receptor. The presence of an intrinsic component in lymphoid cells satisfies this necessity. On the other hand, fibroblasts, which are nonlymphoid cells, do not satisfy this necessity. According to recent researches, the comparison of the number of intermediate affinity binding sites of IL-2 with the number of the binding sites of the β chain of the IL-2 receptor in the case of NK cells in the peripheral blood from a patient who received treatment with IL-2 revealed that the binding site number of IL-2 was far less (Journal of Experimental Medicine, 172, p. 1101, 1990). According to experiments for chemical cross-linking with IL-2 using cells in which a high affinity IL-2 receptor was expressed, various molecules were reported to be able to form a complex with IL-2, including those of a molecular weight of 22 kd or 40 kd (Proceedings of the National Academy of Sciences USA, 87, p. 11, 1990), that of m.w. 64 kd (International Immunology, 2, p. 477, 1990), that of m.w. 70 kd (Proceedings of the National Academy of Sciences USA, 84, p. 2002, 1987; and Nature, 327, p. 518, 1987), that of m.w. 95 kd (Proceedings of National Academy of Sciences USA, 84, p. 7246, 1987), that of m.w. 100 kd (Proceedings of the National Academy of Sciences USA, 87, p. 4869, 1990), and that of m.w. 95–100 kd (journal of Immunology, 145, p. 155, 1990). Eventually, discussion as to the existence of molecules other than the α and β chains are in a state of chaos to such an extent that it has not yet been concluded whether a third molecule actually exists.

Thus, a structural elucidation of the IL-2 receptor has been made impossible.

Investigation and exact understanding of the mechanism of transduction of signals of IL-2 which plays a major role in the immune response are also required for a clarification of the pathogenetic mechanism and therapy of the diseases mentioned above. For this, first it is necessary to draw a definite conclusion as to whether a third IL-2 receptor molecule exists which directs the signal transduction as a constituent molecule of the IL-2 receptor (hereunder referred to as the IL-2 receptor γ chain molecule), and then the IL-2/IL-2 receptor system should be clarified indirectly on a molecular level.

To date, however, although reports have suggested the existence of an IL-2 receptor γ chain molecule, various views have been presented for the substance of the IL-2 receptor γ chain. Actually its molecular weight has not been determined yet, and it is entirely unclear even as to its existence, much more concerning the role of the third molecule for exertion of the function of IL-2. Accordingly, now worldwide competitions are being made for the isolation of its gene, expression of the protein molecule and analysis of the function of the molecule, leading to the finding of a direct evidence for the existence of the γ chain molecule.

SUBJECT MATTER OF THE INVENTION

Briefly, the object of the present invention is to provide a IL-2 receptor γ chain molecule, particularly human IL-2 receptor γ chain molecule, which directs transduction of signals from human IL-2, a human IL-2 receptor γ chain molecule, a gene encoding the IL-2 receptor γ chain molecule, a vector containing said gene, a cell transformed with said vector, a method for the production of a IL-2 receptor γ chain molecule by culturing said cell, an immune response regulatory agent comprising a IL-2 receptor γ chain molecule, a method for detection or assay of the gene encoding a IL-2 receptor γ chain molecule, an antibody capable of binding to an IL-2 receptor γ chain molecule, an immune response regulatory agent which comprises said antibody, and is effective to cure autoimmune diseases and to prevent graft rejection, and a method for the detection or assay of an IL-2 receptor γ chain molecule by using said antibody.

In order to accomplish the subject matter previously described, the inventors of the present invention carried out diligent and extensive studies. As a result, there was found the desired human IL-2 receptor γ chain molecule, a DNA sequence said human IL-2 receptor γ chain molecule, a plasmid vector possessing said DNA sequence, a cell transformed with said vector, a method for the production of human IL-2 receptor γ chain molecule, which comprises culturing of said transformed cell, and an antibody capable of binding to human IL-2 receptor γ chain molecule, and thus the present invention has been accomplished. Hereunder, a detailed explanation will be given regarding the present invention. First, for separation and purification of the human IL-2 receptor γ molecule from the cell surface, MOLT4 cells, a human T lymphocyte cell line, were employed, wherein the α and β chains of the IL-2 receptor are thought not to have been expressed, but high level expression is thought to have been established for the γ chain. Then, cells into which the cDNA for the β chain was transfected with a vector for expression in eucaryotes are prepared (hereunder referred to as MOLT β cells).

Here, as long as the IL-2 receptor β and γ chains are expressed, any human cell may be used for the separation and purification of the IL-2 receptor γ chain molecule. This may also be accomplished by use of other cells than human, which satisfy the above requirement, thus enabling the separation and purification of the IL-2 receptor γ chain molecule from other species. A cell on which only the γ chain is originally exposed is used as a host. Transfectants having incorporated an expression vector containing the cDNA for the β chain may be used. It is added for confirmation only that any human cells other than MOLT4 cells on which only the γ chain is expressed, may be used.

Incidentally, the method for the genetic transduction includes electroporation, potassium phosphate co-precipitation, DEAE dextran, lipofection and any other method with which the desired gene may be transfected (Molecular Cloning, 3rd edition). Electroporation is preferably employed because it provided efficient transfection of the cDNA for the β chain.

Next, MOLT β cells are solubilized after their reaction with human recombinant IL-2. The solubilizing agent available for this use is a detergent such as NONIDET® P-40 (ethylphenylpolyethylene glycol), TRITON® X-100 (octoxynol) etc.

Of course, other detergents may be used. From this solubilized cell fraction is separated a complex consisting of the three molecules: i.e. the IL-2 molecule, the IL-2 receptor β chain molecule and the γ chain molecule. Any other method may be used for the separation, but usually affinity chromatography is preferred.

The affinity chromatography may be carried out by immobilizing an anti-human IL-2 antibody or anti-human IL-2 receptor β chain antibody on a carrier. Here, the anti-human IL-2 antibody or anti-human IL-2 receptor β chain antibody should be such that it does not prevent binding of the respective other antibody, that is, an antibody which does not recognize the respective binding site itself should be used. The kind of animal used as the antibody source does not matter. Further, the antibody may be a polyclonal one, but a monoclonal antibody is recommended.

The supporting agent on which the antibody is immobilized includes agarose gel, polyacrylamide gel or the like, and embodiments of the activating agent to be used includes cyanogen bromide (in the case of agarose gel) and glutaraldehyde (in the case of polyacrylamide gel). Needless to say, the above listed embodiments are only examples of the supporting agent and activating agent, and others may be used.

We conducted earnest and extensive research and prepared many monoclonal anti-IL-2 receptor β chain antibodies. We conducted the selection on antibodies which do not prevent binding of IL-2 to the IL-2 receptor β chain. Then, of the selected ones was selected the most appropriate antibody for the separation and purification of a complex consisting of the IL-2 molecule, the IL-2 receptor β chain molecule and the γ chain molecule, which antibody was subjected to affinity chromatography for separation and purification of an adequate amount of the complex.

Actually, antibody-bound beads and a solubilized cell fraction were mixed for reaction, then the beads were washed thoroughly to elute the three molecules bound to the beads: the IL-2 molecule, the IL-2 receptor β chain molecule and the γ chain molecule. As the elution agent, an acid, an alkali, a protein denaturant, a salt at a high concentration, an ionic detergent, an organic solvent, etc. may be used. In the case where polyacrylamide gel electrophoresis is conducted after the elution for separation of the three molecules, urea or the like is preferred since it has little influence on the electrophoresis.

Next, the eluate is subjected to electrophoresis to separate the IL-2 receptor γ chain molecule. Any electrophoresis including SDS polyacrylamide gel electrophoresis, isoelectric focusing and so forth, may be carried out as long as the three components are separated. However, two dimensional electrophoresis (isoelectric focusing for the first, and SDS electrophoresis for the second) is prefereably effected to ensure complete separation.

After electrophoresis, a protein containing the IL-2 receptor γ chain molecule is electrically transferred from the polyacrylamide gel to a polyvinyliden difluoride (PVDE) membrane, and the site on which the IL-2 receptor γ chain molecule is transferred to is cut off. Here, in order to identify beforehand the site on which the IL-2 receptor γ chain molecule is transferred to, it is recommended to use another gel prepared under the same conditions, subject a portion of the elution fraction to electrophoresis under the same conditions and determine the respective site by protein staining.

Thereafter, the cut-off membrane carrying the transferred IL-2 receptor γ chain molecule is subjected to a vapor phase amino acid sequencer to determine the amino acid sequence from the N-terminus of the IL-2 receptor γ chain molecule. In this connection, the N-terminal amino acid sequence of the IL-2 receptor γ chain molecule was finally determined on the basis of the information from both, the above mentioned amino acid analysis and the sequence of the cDNA, and is listed as Sequence Identification No. 12 in the Sequence Listing.

The present invention is the first success in the world of the purification of the human IL-2 receptor γ chain molecule which is substantially free from the other human proteins and of the determination of the amino acid sequence of its N-terminus.

On the basis of the determined amino acid sequence, all possible DNA sequences were deduced which were thought to correspond to it, and 4 mixtures of DNA oligomers of the N-terminal (5'-end) 17mer (corres. to oligomers Nos. 1–4 in FIG. 1 [Sequence Identification Nos. 13–16]) and 2 mixtures of DNA oligomers of the C-terminal (3'-end) 22mer (of complementary sequences, corresponding to oligomers Nos. 5, 6 in FIG. 1 [Sequence Identification Nos. 17–18]) were designed and synthesized with a DNA synthesizer. Here, the sites of the oligomers to be designed are not limited to these, and any site is available so far as the interstitial distance between the oligomers is over a certain level (around 15mer), and the lengths of the oligomers may be any of 15mer or more, provided that, for the 3'-end primer, the complementary sequence to the original must be designed in the direction from the 3'-end to the 5'-end.

Separately from the above, messenger RNA is prepared from MOLT β cells, and an oligo dT or random hexamer is used as a primer to prepare cDNA and a cDNA library. Any cell on which the human IL-2 receptor γ chain molecule is expressed may be used for collection of the messenger RNA (mRNA).

Incidentally, the preparation of the messenger RNA may be performed with an oligo dT cellulose column after the entire RNA fraction is harvested according to the guanidine thiocyanate method (Biochemistry, 13, p. 2633, 1974). A phage vector such as λgt10, λgt11 or λZAPII or a plasmid vector such as pBR or pUC may be used to prepare the cDNA library.

With the prepared cDNA a polymerase chain reaction (PCR) (Science, 230, p. 1350, 1985) was carried out using the above synthesized DNA oligomer as a primer and Taq polymerase, then the amplified cDNA was recovered.

The thus recovered, amplified cDNA was labelled with $^{32}P$ for the preparation of a probe, and a clone containing the cDNA for the IL-2 receptor γ chain was harvested from the cDNA library mentioned above, and its base sequence was determined by the dideoxy method (Science, 214, p. 1205, 1981).

The base sequence of the IL-2 receptor γ chain molecule and its structure deduced from said base sequence are shown as Sequence Identification No. 3 in the Sequence Listing. This IL-2 receptor γ chain molecule was found to have an open reading frame consisting of 369 amino acids (Sequence Identification No. 4), of which 22 amino acids represent a signal sequence, and 347 amino acids correspond to a mature type of the polypeptide.

That is, in the sequence of the Sequence Identification No. 3 in the Sequence Listings, the sequence from the −22nd Met to the −1st Gly corresponds to the signal peptide. The signal peptide encoding gene is from ATG corresponding to the −22nd Met to GGG corresponding to the −1st Gly.

In turn, the mature type of the polypeptide corresponds to from the 1st Leu to the 347th Thr in Sequence Identification No. 3 in the Sequence Listing. The sequence from CTG corresponding to the 1st Leu to ACC corresponding to th 347th Thr is a gene which codes for the mature type of the polypeptide.

In addition, Sequence Identification No. 4 lists the amino acid sequence and Sequence Identification No. 5 shows the corresponding base sequence of a preform consisting of (1) the mature type of the polypeptide and (2) the signal sequence attached thereto, while the amino acid sequence and the corresponding base sequence of the mature type of the polypeptide are shown in the Sequence Identification No. 6 in the Sequence Listing.

It was revealed that, in the mature type of the polypeptide shown in the Sequence Identification No. 3 in the Sequence Listings, the section from the 1st Leu to the 232nd Asn represents an extracellular region, the one from the 233rd Pro to the 261st Leu represents a transmembrane region, and the one from the 262nd Glu to the 347th Thr represents an intracellular region.

Here, in order to confirm that the cDNA for the IL-2 receptor γ0 chain molecule is the very cDNA which encodes a functional IL-2 receptor γ chain molecule, the present cDNA was linked with an expression vector for expression in eucaryotes. After that, (1) a cDNA for the IL-2 receptor γ chain alone, (2) for the β chain alone, (3) for β and γ chains simultaneously, (4) for α and β chains simultaneously, or (5) for the IL-2 receptor α, β and γ chains was transfected at the same time into a human cell where none of the IL-2 receptor α, β and γ chains was expressed. Any expression vector may be used which enables expression in eucaryotes, and, for example, the early promotor vector from simian virus 40 may be utilized.

The cell actually used for the genetic transfection was mouse L929, but, needless to say, other cells may also be used. The same genetic transfection method as the above may be used for other ones. Incidentally, the mouse L929 cell transfected with the cDNA for the IL-2 receptor γ chain (hereunder referred to as Lγ-4) has been deposited with Fermentation Research Institute, Agency of Industrial Science and Technology (Deposit No.: FERM BP-4199). Next, the cells transfected with the respective cDNA were measured for their ability to bind IL-2, binding affinity and internalizing ability. The results of the functional analysis of the present gene product revealed that transfection of only the β chain cDNA failed to provide IL-2 binding, simultaneous transfection of cDNAs for the β and the γ chains provided intermediate affinity as to binding to IL-2 and internalization of the IL-2 signal. Also, with cDNAs for the α and the β chains brought about pseudo high affinity binding, but internalization of the IL-2 signal did not occur, whereas high affinity binding of Il-2 and internalization of the IL-2 signal was accomplished when α, β and γ chains were transfected at the same time. In other words, for the first time it was proven that the γ chain first found according to the present invention is another constituent of the IL-2 receptor in addition to the α chain of 55 kd and the β chain of 75 kd and is involved in signal transduction. Furthermore, for the first time the present gene product was revealed to be the IL-2 receptor γ chain molecule which is indispensable for exerting the functions of IL-2.

Description will be made hereunder of a method for the production of the IL-2 receptor γ chain molecule by genetic engineering.

For the production of the present IL-2 receptor γ chain molecule, expression may be effected using, as the host, an eucaryote such as CHO cells, mouse L929 cells or the like or a procaryote including E. coli. Here, appropriate choice of an expressible vector depending on each host may be made. Usually an eucaryote is a better host for the expression of the IL-2 receptor γ chain molecule than a procaryote. Now, when the mature type of the IL-2 receptor γ chain molecule which has the amino acid sequence shown in the Sequence Identification No. 7 in the Sequence Listing is intended to be produced, a gene may be used which corresponds to the amino acid sequence shown in the Sequence Identification No. 5 in the Sequence Listing. More particularly, a gene constructed by attaching a stop codon to a gene which codes for the amino acid sequence from the −22nd Met to the 347th Thr shown as the Sequence Identification No. 5 in the Sequence Listing may be used. Here, the base sequence of the gene is not limited to any particular one so far as it corresponds to the amino acid sequence listed in the Sequence Identification No. 5 in the Sequence Listing. Therefore, a natural one (cDNA sequence), or any gene prepared by synthesis may be employed.

Nevertheless, the use of the gene listed in the Sequence Identification No. 5 in the Sequence Listing is preferred. Here, the gene listed in the Sequence Identification No. 5 in the Sequence Listing is the cDNA for the IL-2 receptor γ chain molecule.

For confirmation only, no trouble is caused by use of the gene listed in the Sequence Identification No. 5 in the Sequence Listing because the sequence comprises a stop codon, TGA, whereas attention has to be paid to putting a stop codon after the codon corresponding to the 347th Thr if a synthetic gene is employed. In the case of the production of the mature type of the IL-2 receptor γ chain molecule which possesses the amino acid sequence listed in Sequence Identification No. 7 in the Sequence Listing, using a procaryote such as E. coli, the gene encoding the amino acid sequence listed as the Sequence Identification No. 7 in the Sequence Listing should be inserted between the initiation codon ATG and an appropriate stop codon. Of course, also for this case, the gene encoding the amino acid sequence listed as the Sequence Identification No. 7 in the Sequence Listing may be used as a base sequence other than the natural one as Sequence Identification No. 7 in the Sequence Listing.

The use of the natural sequence shown in the Sequence Identification No. 6 in the Sequence Listing is, however, preferred.

Both, the IL-2 receptor γ chain molecule which is soluble in an aqueous solution (in the present invention this is defined to be the mature type of IL-2 receptor γ chain molecule which lacks the transmembrane and cytoplasmic regions, hereunder referred to as the "soluble IL-2 receptor γ chain molecule" and the gene which codes for the soluble IL-2 receptor γ chain molecule were prepared for the first time in the world. In order to produce the soluble IL-2 receptor γ chain molecule, a cDNA is prepared which has a stop codon incorporated, near the 3'-end of the site which codes for the extracellular region of the IL-2 receptor γ chain, and it is inserted into an expression vector in the same manner as above, and expression may be conducted in an eucaryote such as a CHO cell or a mouse L929 cell or a procaryote such as E. coli. The host cell may be any of eucaryotes and procaryotes, however, the former being employed with advantages.

According to the present invention, the gene encoding the soluble IL-2 receptor γ chain molecule was prepared by putting a stop codon, TAG, after the AAA which encodes the 230th Lys (see the base sequence listed as the Sequence Identification No. 8 in the Sequence Listings).

The amino acid sequence of the soluble IL-2 receptor γ chain molecule is shown as the sequence Identification No. 11 in the Sequence Listing. In addition, the amino acid sequence of the precursor with a signal peptide bound thereto is shown as the Sequence Identification No. 8 in the Sequence Listings. For clarification only, the signal peptide is constituted from the −22nd Met to the −1st Gly of the precursor, while the sequence from the 1st Leu to the 230th Lys being for the desired molecule.

In order to produce the soluble IL-2 receptor γ chain molecule by use of an eucaryote such as CHO cells, mouse L929 cells or the like, a gene constructed by joining an appropriate stop codon to a gene encoding the amino acid sequence shown in Sequence Identification No. 8 in the Sequence Listing may be used.

The base sequence of the gene used may be arbitrary so far as it exactly corresponds to the amino acid sequence as shown as Sequence Identification No. 8 in the Sequence Listing.

Namely there is no need to limit the use of a cloned natural gene only. None the less, the use of the base sequence shown as Sequence Identification No. 8 in the Sequence Listing, namely the naturally ocurring DNA sequence, is preferably used.

For the production of the soluble IL-2 receptor γ chain molecule which utilizes a procaryote such as E. coli, a gene which encodes the amino acid sequence listed in the Sequence Identification No. 11 in the Sequence Listing should be inserted between the initiation codon ATG and an appropriate stop codon.

Of course it is not necessary that the base sequence of the gene which encodes the amino acid sequence shown as the Sequence Identification No. 11 in the Sequence Listing should be the natural one as shown in Sequence Identification No. 10 in the Sequence Listing.

But, the natural sequence shown in the Sequence Identification No. 10 in the Sequence Listing is recommended to be used.

By the way, the conditions for the culture medium and culturing when the host is cultured to produce the desired IL-2 receptor γ chain molecule or the soluble IL-2 receptor γ chain molecule may be conventional.

Concretely, L broth or the like may be used when the host is a procaryote such as E. coli, and the culturing conditions are usually 37° C. for about 12–16 hours.

If the host is an eucaryote, for example, CHO cells, mouse L929 cells or the like, then Dulbecco's Modified Eagle Medium which contains 10% fetal bovine serum or the like, may be used. There is no need to be limited to any particular culturing conditions, but usually the culturing is carried out in the presence of 5% $CO_2$ at 37° C. for 3–4 days.

Any conventional purification method may be employed for the purification of the thus harvested IL-2 receptor γ chain molecule or soluble IL-2 receptor γ chain molecule. In an illustrative purification method, ion exchange chromatography, reverse phase chromatography, chromatofocusing, gel filtration, SDS electrophoresis, etc. may be used alone or in combination.

As mentioned above, there may be produced a recombinant human IL-2 receptor γ chain molecule which contains no substantial amount of the other human proteins. This recombinant human IL-2 receptor γ chain molecule which is substantially free of the other human proteins may be utilized as a medicine such as an immune response regulatory agent, as will be mentioned later.

According to the present invention, the human IL-2 receptor γ chain molecule is not limited to amino acid sequences shown in Sequence Identification Nos. 7 and 11 in the Sequence Listing, and includes all the polypeptides which possess the activity of the human IL-2 receptor γ chain molecule. Therefore, (1) partially converted or (2) substituted versions or (3) one or more N- or C-terminal amino acid addition versions of the amino acid sequence shown in the Sequence Identification No. 7 or 11 in the Sequence Listing are included in the human IL-2 receptor γ chain molecule according to the present invention, so far as they substantially preserve the activity of the human IL-2 receptor γ chain molecule.

Further, as long as the activity of the human IL-2 receptor γ chain molecule is substantially maintained, those which received treatment of the polypeptide chain with polyethylene addition, acetylation or amidation are included in the human IL-2 receptor γ chain molecule of the present invention. The method for the production of the human IL-2 receptor γ chain molecule is not limited to genetic recombination, and chemical synthesis such as solid phase method may also be utilized.

The IL-2 receptor γ chain molecule according to the present invention, particularly the human one, may be used as an immune response regulatory agent. That is, the present invention relates to an immune response regulatory agent which contains a therapeutically effective amount of an IL-2 receptor γ chain molecule.

The content of an IL-2 receptor γ chain molecule in an immune response regulatory agent which contains an IL-2 receptor γ chain molecule, is usually 0.1–100% by weight, preferably 0.5–70% by weight per 100% by weight of the immune response regulatory agent. If necessary, a stabilizing agent such as mannitol or a diluent may be added thereto.

The present immune response regulatory agent may be administered orally, but administration of injections via the parenteral route is desired. Needless to say, the agent intended for parenteral administration is desired to be prepared in a form suitable for such administration.

The dosage for human adults is usually 0.001–1000 mg, preferably 0.01–10 mg per day. Of course, the above dosage is only a standard, more or less dosage may be appropriately selected by depending on the condition of the disease, body weight, etc.

The diseases to which the immune response regulatory agent according to the present invention which contains an IL-2 receptor γ chain molecule may be applied, include rheumatoid arthritis, rejection at the time of organ transplantation, etc., without being limited thereto.

The cDNA for the present IL-2 receptor γ chain may be utilized also for detection and assay of a gene of an IL-2 receptor γ chain which is present in cells, tissues, etc. Concretely, the present cDNA labelled with an isotope such as $^{32}P$ or biotin is used as a probe, and Southern blot technique (Journal of Molecular Biology, 98, p. 503, 1975) may be used for detection and assay of DNA, while Northern blot technique (Proceedings of the National Academy of Sciences USA, 77, p. 5201, 1980), etc. may be used in the case of RNA.

For the preparation of an antibody to the present IL-2 receptor γ chain, the IL-2 receptor γ chain molecule separated and purified according to the manner mentioned above may be used as the antigen. In case of the human IL-2 receptor γ chain molecule the antibody may be effectively obtained by using a cell for immunisation, which is from the same species but different from humans and which is transfected with the DNA for the pesent humans IL-2 receptor γ chain as the antigen. Particularly, the screening becomes easier when a monoclonal antibody is used.

Further, a peptide comprising the sequence shown as the Sequence Identification No. 12 in the Sequence Listing which corresponds to the N-terminal sequence of the human IL-2 receptor γ chain molecule my be synthesized, for example, with a peptide synthesizer, and may be combined with another carrier protein such as bovine serum albumin for use as the antigen. In addition, a sequence corresponding to a portion of the amino acid sequence shown as the Sequence Identification No. 7 or 11 in the Sequence Listing may be synthesized, and also its combination with a carrier protein may be used as the antigen. Of course, the antigen may be a polypeptide which comprises the amino acid sequence listed as the Sequence Identification No. 7 or 11 in the Sequence Listing.

The thus prepared anti-human IL-2 receptor γ chain antibody may be labelled with an isotope such as $^{125}I$, an enzyme or biotin and used for detection and assay of human receptor γ chain molecule present on the surface of cells or in the body fluid.

Here, the antibody may be polyclonal, but a monoclonal antibody is preferred.

Among the anti-human IL-2 receptor γ chain antibodies, those capable of inhibiting the binding between IL-2 receptor β and γ chains and preventing the transduction of signals from IL-2 may be used as medicines for diagnosis and treatment of diseases which are considered to advance due to excessive or disordered production of IL-2 and for prevention of rejection at the time of organ transplantation, etc. That is, the present invention also relates to an immune response regulatory agent which contains a therapeutically effective amount of an antibody which is able to bind to an IL-2 receptor γ molecule. The antibody may be polyclonal, but a monoclonal antibody is preferred.

The content of an anti-IL-2 receptor γ chain molecule antibody in an immune response regulatory agent which contains an antibody capable of binding to an IL-2 receptor γ chain molecule, is usually 0.1–100% by weight, and preferably 0.5–70% by weight per 100% by weight of the immune response regulatory agent. If necessary, a stabilizing agent such as mannitol or a diluent may be added thereto.

The present immune response regulatory agent may be administered orally, but administration of injections via a parenteral route is preferred. Needless to say, the agent intended for parenteral administration is preferably pepared in a form suitable for such administration.

The dosage for human adults is usually 0.001–1000 mg, preferably 0.01–10 mg per day. Of course, the above dosage is only a standard, a greater or lesser dosage may be appropriately selected depending on the condition of the disease, body weight, etc.

The immune response regulatory agent according to the present invention which contains an anti-IL-2 receptor γ chain molecule antibody may be applied to various diseases including rheumatoid arthritis, rejection at the time of organ transplantation, etc., without being limited thereto. For application to humans, the anti-IL-2 receptor γ chain antibodies may be artificially modified; for example the constant region (C-region) of the antibody is replaced by that of a human C region, the antibody consists only of a fragment thereof including the variable regions (mini-antibodies) etc.

In addition, a protein with another function, for example, a toxin, may be bonded to these antibodies and fragments thereof and used.

In order to obtain the IL-2 receptor γ chain cDNA, the polypeptide and antibodies against these polypeptides of other species the above described procedure may be used. Furthermore it is possible to utilize the human cDNA or an anti-human IL-2 receptor γ chain antibody obtained according to the above procedure for screening cDNA-libraries (or in case of using antibodies expression libraries) made of mRNA of different species. The methods employed in screening cDNA libraries/expression libraries are well known in the art and do not require a detailled illustration.

A more detailed explanation will be made hereunder regarding the present invention with reference to the drawings and examples.

BRIEF DESCRIPTION OF THE DRAWINGS

FIG. 1 shows the structure of Primers Nos. 1–6 (Sequence Identification Nos. 13–).

FIG. 4 is a drawing which shows internalization of IL-2 by various cells

EXAMPLE 1

Figure 2:
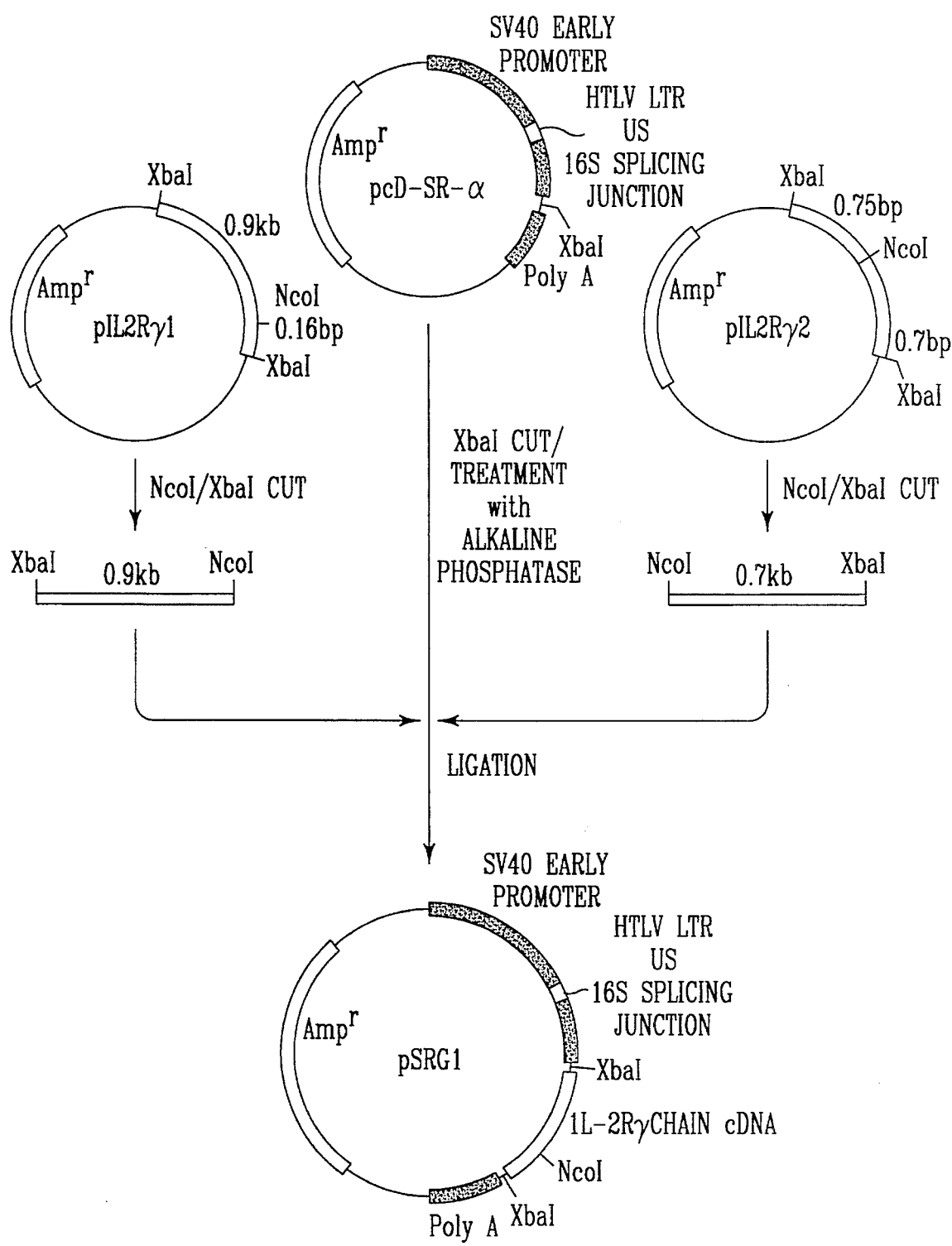
FIG. 2 is a drawing which shows the process for construction of expression vector pSRG1.
Figure 3A:
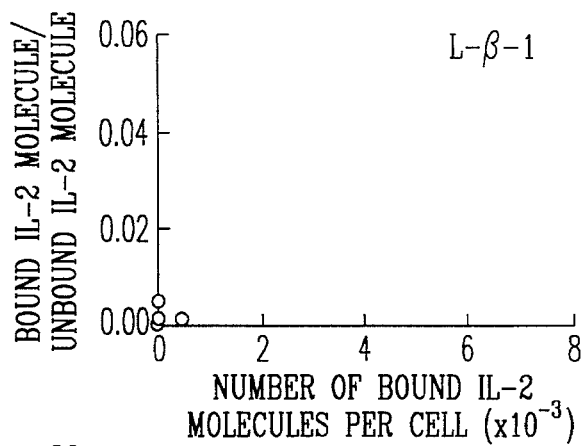
FIG. 3 shows a Scatchard plot which shows the state of IL-2 bound to the receptors on various cells.
Figure 3B:
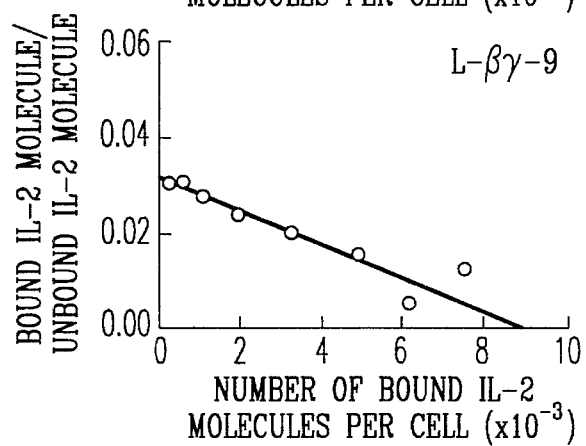
Figure 3C:
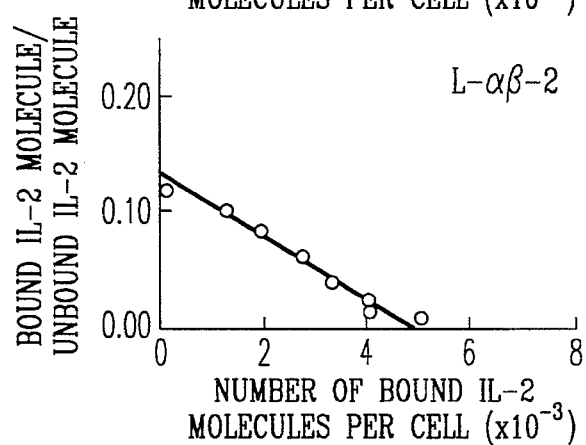
Figure 3D:
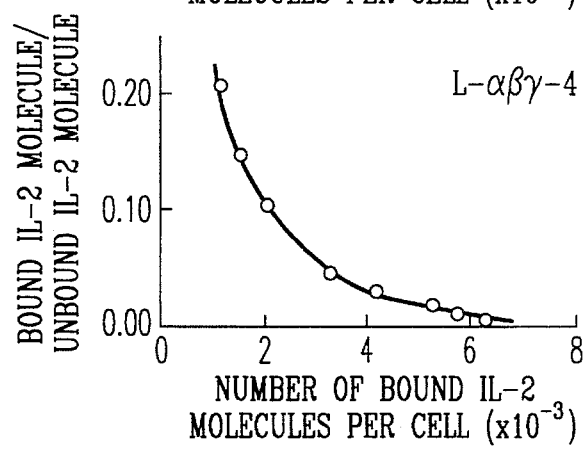

Separation and purification of IL-2 receptor γ chain molecules and determination of the N-terminal amino acid sequence To a pellet of 4×10$^{10}$ MOLT β cells was added 800 ml of a RPMI1640 medium (manufactured by Gibco Inc.) which contains 30 nM of human recombinant IL-2 (manufactured by Ajinomoto Inc.) and 10% fetal bovine serum (manufactured by Hyclone Inc.), and then incubation was carried out at 37° C. for 1 hour.

Next, the cells were subjected to centrifugation (220 g× 10 min.), a pellet was prepared and 800 ml of a buffer solution (0.14M of NaCl, 0.5% NP-40 (NONIDET® P40; ethylphenylpolyethylene glycol), 2 mM of PMSF, 1 mM of EDTA and 20 mM of Tris hydrochloride buffer solution containing 0.1% aprotinin, pH 7.5) was added for solubilization, followed by incubation at 4° C. for 1 hour for cytolysis.

Thereafter, th solubilized cell fraction was charged into a column packed with 1 ml of Affigel 10 (manufactured by Biorad Inc.) at 4° C. at a rate of about 50 ml/min, to which 10 mg of TU11 or a mouse monoclonal anti-IL-2 receptor β chain antibody (International Immunology, 1, p. 373, 1989) had been immobilized per 1 ml of gel beads.

The column was washed first with 300 ml of wash liquid A (0.14M of NaCl, 1% NP-40, 2 mM of EDTA, 0.1% of SDS and 20 mM of Tris hydrochloride buffer solution containing 1% sodium deoxycholate, pH 7.5), then with 300 ml of wash liquid B (0.5M of NaCl, 20 mM of Tris hydrochloride buffer solution containing 1% NP-40, pH 7.5), and finally with 50 ml of wash liquid C (20 mM of Tris hydrochloride buffer solution, pH 7.5).

2 ml of 8M urea was charged into the washed column to elute the IL-2/IL-2 receptor β chain/IL-2 receptor γ chain which had been bound to the column. The eluate was placed in a dialysis tube (manufactured by Sanko-jun-Yaku Inc.), and was allowed to stand under reduced pressure for concentration to 0.4 ml, and this volume was divided into two portions of 0.39 ml and 0.01 ml, each subjected to dimensional polyacrylamide electrophoresis (isoelectric focusing for the first, and SDS electrophoresis for the second). After electrophoresis, the proteins of the eluate (0,39 ml portion), were electrically transferred to an Imobiron P membrane (manufactured by Millipore Inc.). The gel used for electrophoresis of the 0.01 ml of the eluate was subjected to silver staining (manufactured by Dai-Ichi Kagaku Yakuhin Inc.), and the position of IL-2 receptor γ chain molecules after migration was confirmed.

The transfer site of the IL-2 receptor γ chain molecules was cut off from the Imobiron P membrane, and an amino acid sequencer 470A (manufactured by Applied Biosystem Inc.) was employed to determine the 20 N-terminal amino acid residues shown below (Sequence Identification No. 19). Here, the bracketed are possible candidates for which is lacking decisive evidence, and X shows a sequence which could not be identified.

(Leu, Ile)-(Asn, Cys)-(Thr, Phe)-Thr, Phe)-Ile-Leu-Thr-Pro-Asn-Gly-Asn-Glu-(Asp, Arg)-(Thr, Ala)-X-Ala-(Asp, Gly)-Phe-Phe-Leu

EXAMPLE 2

Isolation of a cDNA for a IL-2 receptor γ chain

The entire RNA was separated from 5×10$^6$ MOLT β cells with an RNA extraction kit (manufactured by Pharmacia Inc.). Then a mRNA purification kit (manufactured by Pharmacia Inc.) was used to purify the mRNA. cDNA was synthesized from the purified mRNA, using oligo dT as the primer, and using reverse transcriptase (manufactured by Takara Brewing Inc.).

In view of the N-terminal amino acid sequence of the IL-2 receptor γ chain molecules obtained in Example 1, 6 kinds of oligonucleotides as shown in FIG. 1 (corres. to Primer Nos. 1–6 (Sequence Identification Nos. 13–18) in FIG. 1) were designed and synthesized with a DNA synthesizer 380A (manufactured by Applied Biosystem Inc.). These oligonucleotides were used as the primers for synthesis of the cDNA which was in turn subjected to PCR with Taq polymerase (manufactured by Takara Brewing Inc.) (strand separation at 94° C., annealing at 50° C., strand elongation at 72° C., 30 cycles), using a thermal cycler (manufactured by Perkin Elmer Cetus Inc.).

cDNA amplified by PCR was purified with a MERMAID kit (manufactured by Bio-101 Inc.). cDNA amplified by PCR was purified and labelled with $^{32}$P with a random primer labelling kit (manufactured by Takara Brewing Inc.). This was used as a probe for screening a cDNA library prepared in advance from MOLT β cells using random hexamer as the primer and λ ZAPII as the vector (manufactured by Stratagene Inc.). As a result, a cDNA clone (pIL-2Rγ1) was obtained, and its base sequence was determined with a 7-DEAZA sequencing kit (manufactured by Takara Brewing Inc.). This sequence is shown as Sequence Identification No. 1 in the Sequence Listing.

The present pIL-2Rγ1 was a 3'-end deletion version, so additionally $^{32}$-P-labelled pIL-2Rγ1 was used as a probe to obtain 3 cDNA clones with complete 3'ends (pIL-2Rγ2, pIL-2Rγ3 and pIL-2Rγ4) from a cDNA library which had been prepared in the same manner as the above using oligo dT as the primer, and their base sequences were determined in the same manner (Sequence Identification No. 2 in the Sequence Listing).

In this connection, pIL-Rγ2, pIL-2Rγ3 and pIL-2Rγ4 all had the same base sequence, so the sequence of only pIL-2Rγ2 with the longest 5'-end sequence is listed as Sequence Identification No. 2 in the Sequence Listing.

The entire base sequence of the IL-2 receptor γ chain molecule was determined in consideration of the thus clarified sequences of pIL-2Rγ1 and pIL-2γ2 in combination.

The sequence of cDNA for IL-2 receptor γ chain molecule is listed as Sequence Identification No. 3 in the Sequence Listings. In addition, the amino acid sequence which was presumed based on the base sequence is listed as Sequence Identification No. 3 in the Sequence Listing.

As a result, it was revealed that the present IL-2 receptor γ chain molecule comprises an open reading frame of 369 amino acids, (Sequence Identification No. 4) 22 of which being for the signal sequence, and the sequence of the mature type of the protein consists of 347 amino acids.

That is, in the sequence listed as Sequence Identification No. 4 in the Sequence Listing, the signal peptide corresponds to the section from Met at the −22nd position to Gly at the −1st position. The sequence from ATG corresponding to Met at the −22nd position to GGG which corresponds to Gly at the −1st position is the gene which encodes the signal peptide.

The mature type of polypeptide corresponds to the section from Leu at the 1st position to Thr at the 347th position. The gene which encodes the mature type of the polypeptide is the sequence from CTG corresponding to Leu at the 1st position to ACC which corresponds to Thr at the 347th position in Sequence Identification No. 3 in the Sequence Listing. Incidentally, *E. coli* which had been transformed with the vector including the cDNA for the IL-2 receptor γ chain molecule, i.e. the sequence listed as Sequence Identification No. 3 in the Sequence Listings, has been deposited with the Fermentation Research Institute, Agency of Industrial Science and Technology (Deposit No.: AJ12706, FERM BP-4200).

Further it was revealed that the extracellular region, the transmembrane region and the intracellular region of the IL-2 receptor γ chain molecule comprise 232, 29 and 86 amino acids, respectively. In other words, in the mature type of the polypeptide described in Sequence Identification No. 4 in the Sequence Listing, the section from the 1st Leu to the 232nd Asn is the extracellular region, the one from the 233rd Pro to the 261st Leu is the transmembrane region, and the one from the 262nd Glu to the 347th Thr is the intracellular region.

EXAMPLE 3

Binding of IL-2 to cells transfected with an IL-2 receptor γ chain cDNA cDNA clone p-IL-2Rγ1 obtained in Example 2 was cut with restriction enzymes XbaI and NcoI (both manufactured by Takara Brewing Inc.) to prepare a cDNA fragment with 0.9 kb in length, while a cDNA fragment of 0.7 kb was prepared by cutting pII-2Rγ2 with the same restriction enzymes XbaI and NcoI. The two fragments were cut with XbaI, after which each was mixed with the vector pcDSRα the terminal of which had been dephosphorylated with alkaline phosphatase (Takara Brewing Inc.) (Molecular Cellular Biology, 8, p. 466, 1988), and ligation was carried out with T4DNA ligase (Takara Brewing Inc.), thus constructing expression vector pSRG1 (FIG. 2).

The expression vectors pSRA4 having the cDNA for the IL-2 receptor α chain incorporated therein, and pSRB5 having the cDNA for the IL-2 receptor β chain incorporated therein were also constructed in the same manner.

Together with a neomycin-resistance gene, pSRB5 was transfected alone into mouse L929 cells (50 μg/1×10$^7$, 1500 V, 25 μF) using a gene pulser (manufactured by Biorad Inc.), and the same transfection was also conducted using pSRA4 and pSRB5 simultaneously, pSRB5 and pSRG1 simultaneously, and pSRA4, pSRB5 and pSRG1 simultaneously. The cells were cultured for 3 weeks, using Dulbecco's Modified Eagle Medium (manufactured by Gibco Inc.) which contained 1 mg/ml of neomycin and 10% fetal bovine serum, and the cells with the object genes incorporated therein were cloned by limiting dilution, thus harvesting Lβ-1 cells (L929 cells with IL-2 receptor β chain expression), Lβγ-9 cells (L929 cells with IL-2 receptor β and γ chain expression), Lαβ-2 cells (L929 cells with IL-2 receptor α and β chain expression), Lαβγ-4 cells (L929 with IL-2 receptor α, β and γ chain expression).

In the presence or absence of 3 μM of unlabelled IL-2 various concentrations of IL-2 labelled with $^{125}$I (4×10$^6$ dpm/pmole) by the chloramine-T method were added to 2×10$^6$ Lβ-1 cells, Lβγ-9 cells, Lαβ-2 cells and Lαβγ-4 cells, respectively, and a reaction was carried out at 4° C. for 1.5 hours. The radioactivity of $^{125}$I-IL-2 bound or not bound to the cells was determined. The value for the background or the binding radioactivity in the case of addition of unlabelled IL-2 was subtracted from each of the measurements to calculate the binding amounts, the binding ability and the binding affinity of IL-2 to the receptor as determined by a Scatchard plot. FIG. 3 shows the results of the Scatchard plot, while Table 1 lists the binding affinity calculated from the gradient of the graph of the Scatchard plot. IL-2 binding was not observed for Lβ-1 cells or mouse L929 cells expressing (nonlymphoid cells) only human IL-2 receptor β chain, whereas the binding affinity of IL-2 was found to be 4.6 nM, representing an intermediate affinity value for Lβγ-9 cells with both β and γ chain expression, in the same manner as in the case of lymphoid cells. Further, for Lαβ-2 cells with IL-2 receptor α and β chain expression, the binding affinity was a pseudo high affinity of 600 pM. For Lαβγ-4 cells with γ chain expression as well as α and β chain expression, the binding was a biphasic one, of which the high affinity binding was 77 pM, almost equal to that of lymphoid cells. Surely it was proven that the isolated cDNA is the cDNA encoding the IL-2 receptor γ chain molecule present in human lmyphoid cells.

TABLE 1

| Name of cells | Binding affinity |
| --- | --- |
| Lβ-1 | — |
| Lβγ-9 | 4.6 nM |
| Lαβ-2 | 600 pM |
| Lαβγ-4 | 77 pM (high affinitive binding) |
|  | 2.4 nM (low affinitive binding) |

EXAMPLE 4

Internalization of IL-2 by cells transfected with the IL-2 receptor γ chain cDNA Ten nM of $^{125}$I-IL-2 was added to 2×10$^6$ Lβγ-9 cells, Lα'-2 cells, Lαβγ-4 cells, respectively, and the mixture was then reacted at 0° C. for 1 hour, followed by washing with 10 mM of phosphate buffer solution containing 0.15M of NaCl, at pH 7.5 (PBS), to remove $^{125}$I-IL-2 not bound to the cells. Next the cell suspension was incubated at 37° C. sequentially, immediately after which the cells were suspended in cooled 0.2M glycine hydrochloride buffer solution (pH 2.8), and the suspension was allowed to stand for 10 minutes. The amount of the $^{125}$I-IL-2 scaled off into the solution was determined to be that of the $^{125}$I-IL-2 which had been bound to the receptor on the cell membrane, while that of the $^{125}$I-IL-2 left in the cells was deemed to be that of the $^{125}$I-IL-2 in the cells.

As a result, as shown in FIG. 4, the internalization of IL-2 did not occur even with lapse of time, but it was made clear that the IL-2 internalization occurs for Lβγ-9 cells and Lαβγ-4 cells as time goes by.

In other words this result evidences that the presence of the IL-2 receptor γ chain molecule contributes to the internalization of Il-2, the present molecule is involved in transduction of signals from IL-2, and it is thus a molecule indispensable for the funtions of IL-2.

EXAMPLE 5

Preparation of antibodies to the N-terminal peptide of IL-2 receptor γ chain molecule and IL-2 receptor γ chain molecule A peptide corresponding to the N-terminal sequence of the IL-2 receptor γ chain listed as Sequence Identification No. 12 in the Sequence Listing, was synthesized with a peptide synthesizer (Applied Biosystem Inc.). 5 mg of the synthesized peptide was bound to 10 mg of KLH (keyhole limpet hemocyanin manufactured by Wako-Jun-Yaku Inc.) using m-male-imidobenzoyl-N-hydroxysuccinimide ester (Pierece Inc.), and then mixed with Freund's complete adjuvant (manufactured by Difco Inc.) at a proportion of 1:1 to prepare an emulsion, a sixth of which was used for immunization of each rabbit, and a twelfth of which was used for that of each mouse, both by intramuscular injection.

The same operation was repeated twice 2 weeks apart, and for the preparation of a rabbit polyclonal antibody, the blood was taken 7 days after the final immunization, after which the serum was separated. This serum was further subjected to salting out with 40% saturation ammonium sulfate. An IgG fraction was obtained by affinity chromatography using protein A sepharose (manufactured by Pharmacia Inc.). Fifty milliliters of the serum provided 270 mg of the IgG fraction.

Next, in order to prepare a mouse monoclonal antibody, 3 days after the final immunization, mouse spleen cells and myeloma cells (P3X63Ag8.653) were mixed at a portion of 10:1 to induce their fusion in the presence of polyethylene glycol #4000 (manufactured by Flow Inc.), and selection of the fused cells was carried out in RPMI1640 medium which contained a HAT solution (manufactured by Flow Inc.) and 10% fetal bovine serum. The supernatant from the culture of the fused cells was subjected to a reaction in a flexible 96-well flat plate (manufactured by Falcon Inc.) with 10 μg/ml of peptide coated thereon, washed with 10 mM phosphate buffer solution (pH 7.5) containing 0.05% Tween 20 and 0.15M of NaCl, and then reacted with $^{125}$I-labelled anti-mouse immunoglobulin antibody (manufactured by Amersham Inc.) and washing in the same manner. Selection of mouse monoclonal antibody-producing hybridomas for the peptide is made by measuring the radioactivity bound to each well.

Balb/c mice which had been intraperitoneally injected 1 week before with 0.5 ml/mouse of Pristan (manufactured by Wako-Jun-Yaku Inc.) were further injected intraperitoneally with 1×10$^7$ hybridomas per mouse, followed by collection of ascites after 7–10 days. The ascites were subjected to salting out with 40% saturation ammonium sulfate, and an antibody was harvested by affinity chromatography using protein A sepharose. Thirty five grams of the antibody was recovered from 10 ml of the ascites.

For the preparation of an antibody against the IL-2 receptor γ chain molecule, according to the method as shown in Example 3, the cDNA for the IL-2 receptor γ chain was introduced into Balb/3T3 cells, and immunization was accomplished by intraperitoneal injection of cells with IL-2 receptor γ chain molecule expressed thereon at a proportion of 1×10$^7$ cells per Balb/c mouse.

The same procedures were repeated twice each 2 weeks, for the preparation of a polyclonal antibody, the blood was taken 7 days thereafter, followed by separation of the serum.

The obtained serum was then subjected to salting out with 40% saturation ammonium sulfate. After that the IgG fraction was harvested by affinity chromatography using protein A sepharose.

For the preparation of a monoclonal antibody, fused cells are harvested in the same manner as above, 3 days after the final immunization. The supernatant from the culture was reacted with MOLT4 cells, washed with RPMI1640 medium containing 10% fetal bovine serum, followed by reaction with $^{125}$I-labelled anti-mouse immunoglobulin antibody (manufactured by Amersham Inc.) and washing in the same manner. Selection of mouse monoclonal antibody-producing hybridomas for the IL-2 receptor γ chain molecule is made by measuring of the radioactivity bound to the cells. An antibody was harvested in the same manner as the above. Four milligrams of polyclonal antibodies were recovered from 1 ml of the serum, while 23–38 g of a monoclonal antibody was recovered per 10 ml of the ascites.

EXAMPLE 6

Preparation of a soluble Il-2 receptor γ chain

For the preparation of the IL-2 receptor γ chain cDNA with a stop codon at the 3'-terminus in the extracellular region, PCR with Taq polymerase (strand separation at 94° C., annealing at 50° C., strand elongation at 72° C., 20 cycles) was conducted, by using as primers, oligomer 5'-AGCTCGAGCGCCATGTTGAAGCCCAT-3' (Sequence Identification No. 20) and 5'-AACTCGAGAGGATTC-TATTTTGAAGTAT-3'(Sequence Identification No. 21) including an XhoI site, which were synthesized with a DNA synthesizer 380A, and by using a thermal cycler, wherein pSRG1 prepared in Example 3 was used as the sample.

Figure 5:
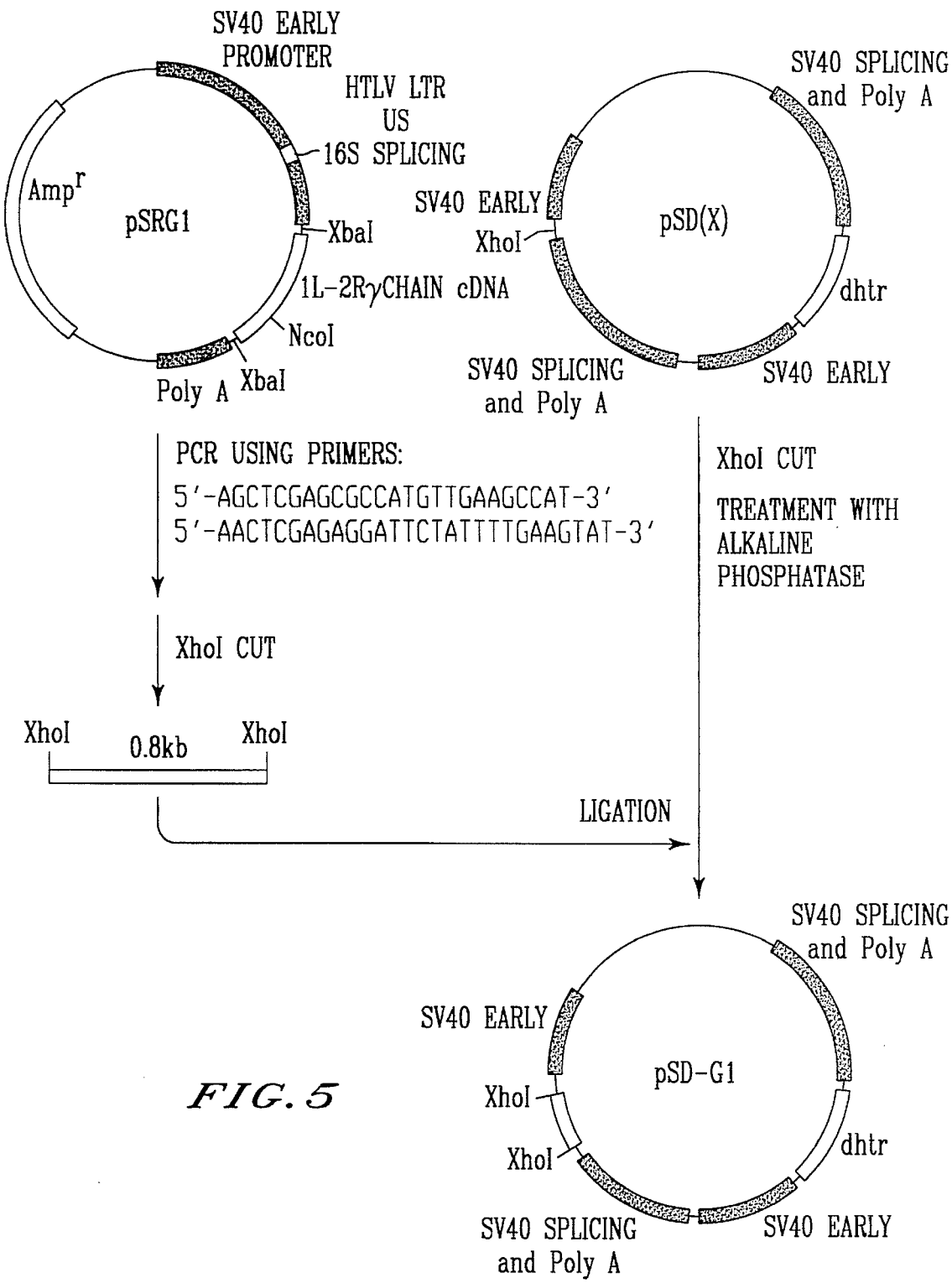
FIG. 5 illustrates the construction of expression vector pSD-G1.

About 0.8 kb of the amplified band was recovered, then cut with XhoI (manufactured by Takara Brewing Inc.), after which ligation was carried out along with pSD(X) vector which had been cut with XhoI and dephosphorylated with alkaline phosphatase at the termini (Proceedings of the National Academy of Sciences USA, 85, p. 2434, 1988). The insertion in the positive direction was selected for construction of pSD-G1. FIG. 5 shows the construction of the expression vector pSD-G1.

The aforementioned operation thus enabled preparation of the sequence with the stop codon TAG inserted after the codon AAA which codes for the 230th Lys, as shown in Sequence Identification No. 8 in the Sequence Listing.

In a 6 cm dish (manufactured by Falcon Inc.) $1.5 \times 10^5$ CHO cells (DHFR$^-$ strain) in the logarithmic phase were scattered, and cultured in αMEM (Gibco Inc.) which contains 10% FCS, 2 mg/ml of NaHCO$_3$ and 100 μg/ml of kanamycin sulfate (Meiji Seika Inc.), at 37° C. for 24 hours. Plasmid pSD-G1 is transduced by the potassium phosphate method (Molecular Cloning, 2nd edition, 1989).

Thereafter, culturing is performed overnight. Then, the medium was replaced by a fresh one for further culturing for 24 hours, after which the cells were divided, and cultured for an additional 24 hour. Next, the medium was replaced by a fresh one of the same composition but lacking nucleic acid, and culturing was effected for 7–10 days for selection of DHFR$^+$ cells.

The supernatant from the culture was reacted in a 96-well flexible plate with a coating of 10 μg/ml of the monoclonal antibody prepared in Example 5, and washed with 10 mM phosphate buffer solution (pH 7.5) containing 0.05% Tween 20 and 0.15M of NaCl, and followed by addition of a monoclonal antibody labelled with $^{125}$I by the chrolamine-T method (an antibody other than that used for the coating) and washed in the same manner. The selection of cells with soluble IL-2 receptor γ chain expression was performed by measurement of the radioactivity bound to each cell.

Fifteen liters of the supernatant from the culture of the strain with high expression of the soluble IL-2 receptor γ chain molecule is concentrated to 1,500 ml, and added to 5 ml of Sepharose 4B (5 mg/ml, manufactured by Pharmacia Inc.) with the anti-IL-2 receptor γ chain antibody prepared in Example 5 bound thereto. The column is washed with 100 ml of PBS, and the bound soluble IL-2 receptor γ chain molecule was eluted with 0.1M of acetic acid (pH 3.1), immediately after which the eluate was neutralized with 1M Tris-HCl buffer solution (pH 7.5), and dialyzed against 50 mM of Tris-HCl buffer solution (pH 8.0) which contains 0.1M of NaCl, for elution of the soluble IL-2 receptor γ chain molecule. The foregoing operation concentrates the soluble IL-2 receptor γ chain molecule to about 10,000 times, and provides a recovery rate of about 70%.

This elution fraction is purified to a high level by reverse phase HPLC using an ODS column (Yamamura Kagaku Inc.). Ten milliliters of the elution fraction is placed in an ODS column equilibrated with 0.1% trifluoroacetic acid (pH 2.0, manufactured by Nakaraitesugue Inc.), and the adsorbed proteins were eluted according to a linear concentration gradient with 0–80% acetonitrile which contains 0.1% trifluoroacetic acid, for separation and purification of the soluble Il-2 receptor γ chain molecule. The present operation concentrates the soluble IL-2 receptor γ chain molecule about 25,000-fold and produces a final recovery rate of 45%.

Analysis with an amino acid analyzer showed that the amino acid sequence of the recovered soluble IL-2 receptor γ chain molecule is the same one listed as Sequence Identification No. 7 in the Sequence Listings.

The IL-2 receptor γ chain molecule and the soluble IL-2 receptor γ chain molecule according to the present invention is a substance which has a wide variety of uses, for example for clarification of the IL-2/IL-2 receptor system or as an immune response regulatory agent, etc.

Moreover, a gene encoding IL-2 receptor γ chain molecule and a gene encoding a soluble IL-2 receptor γ chain molecule are substances which may produce useful IL-2 receptor γ chain molecules and soluble IL-2 receptor γ chain molecules by application of genetic engineering. Furthermore, an antibody to IL-2 receptor γ molecule is also a useful substance, which may be utilized as an immune response regulatory agent, etc.

We claim:

1. Isolated and purified DNA having a nucleotide sequence coding for human interleukin-2 receptor γ-chain, selected from the group consisting of: (a) sequence Id Nos. 1, 2, 3, 5, 6, 8 and 10; and (b) altered nucleotide sequences of (a) due to degeneracy in the genetic code.

2. Isolated and purified DNA having a nucleotide sequence according to claim 1, which is represented by the following nucleotide sequence: (Seq. Id. No. 10)

| | |
|---|---|
| CTG AAC ACG ACA ATT CTG ACG CCC AAT GGG AAT GAA GAC ACC ACA GCT | 48 |
| GAT TTC TTC CTG ACC ACT ATG CCC ACT GAC TCC CTC AGC GTT TCC ACT | 96 |
| CTG CCC CTC CCA GAG GTT CAG TGT TTT GTG TTC AAT GTC GAG TAC ATG | 144 |
| AAT TGC ACT TGG AAC AGC AGC TCT GAG CCC CAG CCT ACC AAC CTC ACT | 192 |
| CTG CAT TAT TGG TAC AAG AAC TCG GAT AAT GAT AAA GTC CAG AAG TGC | 240 |
| AGC CAC TAT CTA TTC TCT GAA GAA ATC ACT TCT GGC TGT CAG TTG CAA | 288 |
| AAA AAG GAG ATC CAC CTC TAC CAA ACA TTT GTT GTT CAG CTC CAG GAC | 336 |
| CCA CGG GAA CCC AGG AGA CAG GCC ACA CAG ATG CTA AAA CTG CAG AAT | 384 |
| CTG GTG ATC CCC TGG GCT CCA GAG AAC CTA ACA CTT CAC AAA CTG AGT | 432 |
| GAA TCC CAG CTA GAA CTG AAC TGG AAC AAC AGA TTC TTG AAC CAC TGT | 480 |
| TTG GAG CAC TTG GTG CAG TAC CGG ACT GAC TGG GAC CAC AGC TGG ACT | 528 |
| GAA CAA TCA GTG GAT TAT AGA CAT AAG TTC TCC TTG CCT AGT GTG GAT | 576 |
| GGG CAG AAA CGC TAC ACG TTT CGT GTT CGG AGC CGC TTT AAC CCA CTC | 624 |
| TGT GGA AGT GCT CAG CAT TGG AGT GAA TGG AGC CAC CCA ATC CAC TGG | 672 |
| GGG AGC AAT ACT TCA AAA TAG | 693 |

3. Isolated and purified DNA having a nucleotide sequence according to claim 1, which is represented by the following nucleotide sequence: (Seq. Id. No. 8)

| | |
|---|---|
| ATG TTG AAG CCA TCA TTA CCA TTC ACA TCC CTC TTA TTC CTG CAG CTG | 48 |
| CCC CTG CTG GGA GTG GGG CTG AAC ACG ACG ATT CTG ACG CCC AAT GGG | 96 |
| AAT GAA GAC ACC ACA GCT GAT TTC TTC CTG ACC ACT ATG CCC ACT GAC | 144 |
| TCC CTC AGC GTT TCC ACT CTG CCC CTC CCA GAG GTT CAG TGT TTT GTG | 192 |
| TTC AAT GTC GAG TAC ATG AAT TGC ACT TGG AAC AGC AGC TCT GAG CCC | 240 |
| CAG CCT ACC AAC CTC ACT CTG CAT TAT TGG TAC AAG AAC TCG GAT AAT | 288 |
| GAT AAA GTC CAG AAG TGC AGC CAC TAT CTA TTC TCT GAA GAA ATC ACT | 336 |
| TCT GGC TGT CAG TTG CAA AAA AAG GAG ATC CAC CTC TAC CAA ACA TTT | 384 |
| GTT GTT CAG CTC CAG GAC CCA CGG GAA CCC AGG AGA CAG GCC ACA CAG | 432 |
| ATG CTA AAA CTG CAG AAT CTG CTG ATC CCC TGG GCT CCA GAG AAC CTA | 480 |
| ACA CTT CAC AAA CTG AGT GAA TCC CAG CTA GAA CTG AAC TGG AAC AAC | 528 |
| AGA TTC TTG AAC CAC TGT TTG GAG CAC TTG GTG CAG TAC CGG ACT GAC | 576 |
| TGG GAC CAC AGC TGG ACT GAA CAA TCA GTG GAT TAT AGA CAT AAG TTC | 624 |
| TCC TTG CCT AGT GTG GAT GGG CAG AAA CGC TAC ACG TTT CGT GTT CGG | 672 |
| AGC CGC TTT AAC CCA CTC TGT GGA AGT GCT CAG CAT TGG AGT GAA TGG | 720 |
| AGC CAC CCA ATC CAC TGG GGG AGC AAT ACT TCA AAA TAG | 759 |

4. Isolated and purified DNA having a nucleotide

| | |
|---|---|
| CTG AAC ACG ACA ATT CTG ACG CCC AAT GTG AAT GAA GAC ACC ACA GCT | 48 |
| GAT TTC TTC CTG ACC ACT ATG CCC ACT GAC TCC CTC AGC GTT TCC ACT | 96 |
| CTG CCC CTC CCA GAG GTT CAG TGT TTT GTG TTC AAT GTC GAG TAC ATG | 144 |
| AAT TGC ACT TGG AAC AGC AGC TCT GAG CCC CAG CCT ACC AAC CTC ACT | 192 |
| AAT TGC ACT TGG AAC AGC AGC TCT GAG CCC CAG CCT ACC AAC CTC ACT | 192 |
| CTG CAT TAT TGG TAC AAG AAC TCT GAT AAT GAT AAA GTC CAG AAG TGC | 240 |
| AGC CAC TAT CTA TTC TCT GAA GAA ATC ACT TCT GGC TGT CAG TTG CAA | 288 |
| AAA AAG GAG ATC CAC CTC TAC CAA ACA TTT GTT GTT CAG CTC CAG GAC | 336 |
| CCA CGG GAA CCC AGG AGA CAG GCC ACA CAG ATG CTA AAA CTG CAG AAT | 384 |
| CTG GTG ATC CCC TGG GCT CCA GAG AAC CTA ACA CTT CAC AAA CTG AGT | 432 |
| GAA TCC CAG CTA GAA CTG AAC TGG AAC AAC AGA TTC TTG AAC CAC TCT | 480 |
| TTG GAG CAC TTG GTG CAG TAC CGG ACT GAC TGG GAC CAC AGC TGG ACT | 528 |

-continued

| | |
|---|---|
| GAA CAA TCA GTG GAT TAT AGA CAT AAG TTC TCC TTT CCT AGT GTG GAT | 576 |
| GGG CAG AAA CGC TAC ACG TTT CCT GTT CGG AGC CGC TTT AAC CCA CTC | 624 |
| TGT GGA AGT GCT CAG CAT TGG AGT GAA TGG AGC CAC CCA ATC CAC TGG | 672 |
| GGG AGC AAT ACT TCA AAA GAG AAT CCT TTC CTG TTT GCA TTG GAA GCC | 720 |
| GTG GTT ATC TCT GTT GGC TCC ATG GGA TTG ATT ATC AGC CTT CTC TGT | 768 |
| GTG TAT TTC TGG CTG GAA CGG ACG ATG CCC CGA ATT CCC ACC CTG AAG | 816 |
| AAC CTA GAG GAT CTT GTT ACT GAA TAC CAC GGG AAC TTT TCG GCC TGG | 864 |
| AGT GGT GTG TCT AAG GGA CTG GCT GAG AGT CTG CAG CCA GAC TAC AGT | 912 |
| GAA CGA CTC TGC CTC GTC AGT GAG ATT CCC CCA AAA GGA GGG GCC CTT | 960 |
| GGG GAG GGG CCT GGG GCC TCC CCA TGC AAC CAG CAT AGC CCC TAC TGG | 1008 |
| GCC CCC CCA TGT TAC ACC CTA AAG CCT GAA ACC TGA | 1044 |

5. Isolated and purified DNA having a nucleotide sequence according to claim 1, which is represented by the following nucleotide sequence: (Seq. Id. No. 5)

| | |
|---|---|
| ATG TTG AAG CCA TCA TTA CCA TTC ACA TCC CTC TTA TTC CTG CAG CTG | 48 |
| CCC CTG CTG GGA GTG GGG CTG AAC ACG ACA ATT CTG ACG CCC AAT GGG | 96 |
| AAT GAA GAC ACC ACA GCT GAT TTC TTC CTG ACC ACT ATG CCC ACT GAC | 144 |
| TCC CTC AGC GTT TCC ACT CTG CCC CTC CCA GAG GTT CAG TGT TTT GTG | 192 |
| TTC AAT GTC GAG TAC ATG AAT TGC ACT TGG AAC AGC AGC TCT GAG CCC | 240 |
| CAG CCT ACC AAC CTC ACT CTG CAT TAT TGG TAC AAG AAC TCG GAT AAT | 288 |
| GAT AAA GTC CAG AAG TGC AGC CAC TAT CTA TTC TCT GAA GAA ATC ACT | 336 |
| TCT GGC TGT CAG TTG CAA AAA AAG GAG ATC CAC CTC TAC CAA ACA TTT | 384 |
| GTT GTT CAG CTC CAG GAC CCA CGG GAA CCC AGG AGA CAG GCC ACA CAG | 432 |
| ATG CTA AAA CTG CAG AAT CTG GTG ATC CCC TGG GCT CCA GAG AAC CTA | 480 |
| ACA CTT CAC AAA CTG AGT GAA TCC CAG CTA GAA CTG AAC TGG AAC AAC | 528 |
| AGA TTC TTG AAC CAC TGT TTG GAG CAC TTG GTG CAG TAC CGG ACT GAC | 576 |
| TGG GAC CAC AGC TGG ACT GAA CAA TCA GTG GAT TAT AGA CAT AAG TTC | 624 |
| TCC TTG CCT AGT GTG GAT GGG CAG AAA CGC TAC ACG TTT CGT GTT CGG | 672 |
| AGC CGC TTT AAC CCT CTC TCT GGA AGT GCT CAG CAT TGG AGT GAA TGG | 720 |
| AGC CAC CCA ATC CAC TGG GGG AGC AAT ACT TCA AAA GAG AAT CCT TTC | 768 |
| CTG TTT GCA TTG GAA GCC GTG GTT ATC TCT GTT GGC TCC ATG GGA TTG | 816 |
| ATT ATC AGC CTT CTC TGT GTG TAT TTC TGG CTG GAA CGG ACG ATG CCC | 864 |
| CGA ATT CCC ACC CTG AAG AAC CTA GAG GAT CTT GTT ACT GAA TAC CAC | 912 |
| GGG AAC TTT TCG GCC TGG AGT GGT GTG TCT AAG GGA CTG GCT GAG AGT | 960 |
| CTG CAG CCA GAC TAC AGT GAA CGA CTC TGC CTC GTC AGT GAG ATT CCC | 1008 |
| CCA AAA GGA GGG GCC CTT GGG GAG GGG CCT GGG GCC TCC CCA TGC AAC | 1056 |
| CAG CAT AGC CCC TAC TGG GCC CCC CCA TGT TAC ACC CTA AAG CCT GAA | 1104 |
| ACC TGA | 1110 |

6. A vector comprising DNA according to claim 1.

7. A vector according to claim 6, which is an expression vector.

8. A vector according to claim 6, which can be propagated in an eucaryotic cell.

9. A vector according to claim 6, which can be propagated in an procaryotic cell.

10. A cell transformed with a vector according to claim 6.

11. A cell according to claim 10, which is FERM BP-4199.

12. A cell according to claim 10, which is FERM BP-4200.

13. A cell transformed with DNA according to claim 1.

14. A cell according to claim 13, which is an eucaryotic cell.

15. A cell according to claim 13, which is an procaryotic cell.

16. A cell according to claim 14, which is a CHO cell.

17. A cell according to claim 14, which is a mouse L929 cell.

18. A cell according to claim 15, which is of the genus *E. coli*.

* * * * *

UNITED STATES PATENT AND TRADEMARK OFFICE
CERTIFICATE OF CORRECTION

PATENT NO. : 5,510,259

DATED : April 23, 1996

INVENTOR(S) : KAZUO SUGAMURA ET AL

It is certified that error appears in the above-identified patent and that said Letters Patent is hereby corrected as shown below:

Column 1, line 35, "immunocompetenT-cells" should read --immunocompetent T-cells--.

Column 1, line 39, "charac-terized" should read --characterized--.

Column 2, line 33, "internalising" should read --internalizing--.

Column 2, line 63, "journal" should read --Journal--.

Column 5, line 7, "prefereably" should read --preferably--.

Column 6, line 23, "to th" should read --to the--.

Column 6, line 43, "receptor $\gamma 0$ chain" should read --receptor $\gamma$ chain--.

Column 7, line 6, "Il-2" should read --IL-2--.

Column 8, line 44, "ocurring" should read --occurring--.

Column 10, line 19, "immunisation" should read --immunization--.

UNITED STATES PATENT AND TRADEMARK OFFICE
CERTIFICATE OF CORRECTION

PATENT NO. : 5,510,259

DATED : April 23, 1996

INVENTOR(S) : KAZUO SUGAMURA ET AL

It is certified that error appears in the above-identified patent and that said Letters Patent is hereby corrected as shown below:

Column 10, line 27, "my" should read --may--.

Column 11, line 31, "detailled" should read --detailed--.

Column 11, line 39, "Nos. 13-)" should read --Nos. 13-18)--.

Column 12, line 3, "th solubilized" should read --the solubilized--.

Column 12, line 26, "(0,39 ml portion)" should read --(0.39 ml portion)--.

Column 13, line 32, "Listings" should read --Listing--.

Column 15, line 18, "L$\alpha$-2" should read --L$\alpha\beta$-2--.

Column 15, line 38, "Il-2" should read --IL-2--.

Column 17, line 30, "hour" should read --hours--.

UNITED STATES PATENT AND TRADEMARK OFFICE
CERTIFICATE OF CORRECTION

PATENT NO.   : 5,510,259
DATED        : April 23, 1996
INVENTOR(S)  : Kazuo Sugamura, et. al.

It is certified that error appears in the above-indentified patent and that said Letters Patent is hereby corrected as shown below:

Column 18, line 29, "Listings" should read --Listing--.

Signed and Sealed this

Eighteenth Day of November 1997

Attest:

BRUCE LEHMAN

Attesting Officer

Commissioner of Patents and Trademarks